US011445928B2

(12) United States Patent
Meyer et al.

(10) Patent No.: US 11,445,928 B2
(45) Date of Patent: Sep. 20, 2022

(54) CONFIGURATION DETECTION FOR A SENSOR ASSEMBLY

(71) Applicant: Murata Vios, Inc., Woodbury, MN (US)

(72) Inventors: Benjamin David Meyer, Woodbury, MN (US); Scott Thomas Mazar, Woodbury, MN (US)

(73) Assignee: MURATA VIOS, INC., Woodbury, MN (US)

( * ) Notice: Subject to any disclaimer, the term of this patent is extended or adjusted under 35 U.S.C. 154(b) by 52 days.

(21) Appl. No.: 16/690,457

(22) Filed: Nov. 21, 2019

(65) Prior Publication Data

US 2020/0163563 A1 May 28, 2020

Related U.S. Application Data

(60) Provisional application No. 62/771,405, filed on Nov. 26, 2018.

(51) Int. Cl.
*A61B 5/00* (2006.01)
*A61B 5/0205* (2006.01)
*A61B 5/024* (2006.01)

(52) U.S. Cl.
CPC ........ *A61B 5/02438* (2013.01); *A61B 5/0002* (2013.01); *A61B 5/0205* (2013.01); *A61B 2562/0271* (2013.01); *A61B 2562/08* (2013.01)

(58) Field of Classification Search
CPC . A61B 5/02438; A61B 5/0002; A61B 5/0205; A61B 2562/0271; A61B 2562/08; A61B 5/01; A61B 2562/16
See application file for complete search history.

(56) References Cited

U.S. PATENT DOCUMENTS 6,349,228 B1 * 2/2002 Kiani ................. A61B 5/14551
600/323
7,257,438 B2 8/2007 Kinast
(Continued)

FOREIGN PATENT DOCUMENTS

JP 2008-544776 A 12/2008
JP 2012-505707 A 3/2012
(Continued)

OTHER PUBLICATIONS

Official Communication issued in corresponding Chinese Patent Application No. 201911166230.4, dated May 30, 2022.

*Primary Examiner* — Brian T Gedeon
*Assistant Examiner* — Joshua Andrew Schum-Houck
(74) *Attorney, Agent, or Firm* — Keating & Bennett, LLP

(57) ABSTRACT

Methods, systems, and apparatus for detecting configuration for a patient worn sensor assembly are described. In one aspect a method includes receiving, by a computer system, sensor assembly data for a particular sensor assembly, accessing, by the computer system, sensor assembly identifier information defining a plurality of sensor assembly identifiers, where each sensor assembly identifier is associated with a respective sensor assembly, identifying, by the computer system and based on the sensor assembly data, a particular sensor assembly identifier for the particular sensor assembly, and determining, by the computer system, configuration information for the particular sensor assembly based on the particular sensor assembly identifier.

8 Claims, 14 Drawing Sheets

(56) References Cited

U.S. PATENT DOCUMENTS

| | | | |
|---|---|---|---|
| 7,509,494 B2* | 3/2009 | Al-Ali | A61B 5/14551 600/310 |
| 9,138,180 B1* | 9/2015 | Coverston | H01R 27/00 |
| 10,226,187 B2 | 3/2019 | Al-Ali | |
| 2003/0050545 A1* | 3/2003 | Hicks | A61B 5/6838 600/322 |
| 2010/0191074 A1* | 7/2010 | Chou | G16H 40/67 600/301 |
| 2011/0087129 A1* | 4/2011 | Chetham | A61B 5/7203 600/547 |
| 2012/0029304 A1* | 2/2012 | Medina | A61B 5/02055 600/300 |
| 2012/0095360 A1 | 4/2012 | Runney et al. | |
| 2015/0120004 A1 | 4/2015 | Jimi et al. | |
| 2016/0021219 A1* | 1/2016 | Brown | A61B 6/566 370/216 |
| 2016/0270668 A1* | 9/2016 | Gil | A61B 5/021 |
| 2017/0196511 A1* | 7/2017 | Ehret | A61B 5/6803 |
| 2017/0344451 A1* | 11/2017 | Vanderah | G06F 13/4068 |
| 2018/0158542 A1 | 6/2018 | Kim et al. | |

FOREIGN PATENT DOCUMENTS

| | | |
|---|---|---|
| KR | 10-2016-0125813 A | 11/2016 |
| WO | WO 2015160643 | 10/2015 |

* cited by examiner

CONFIGURATION DETECTION FOR A SENSOR ASSEMBLY

CROSS-REFERENCE TO RELATED APPLICATIONS

This application claims the benefit of U.S. Provisional Application Ser. No. 62/771,405, filed on Nov. 26, 2018, the content of this aforementioned application being fully incorporated herein by reference.

BACKGROUND

Many different types of patient monitoring systems require a direct electrical interface to the skin of a patient. In some applications, the direct electrical interface to the patient's skin is for sensing electrical information present at that skin location, while in other applications, the direct electrical interface is for injecting an electrical current signal at that skin location. One example of a device with a skin electrical interface is a patient-worn sensor device that, among other capabilities, may collect patient electrocardiogram ("ECG") information sensed at the skin of the patient and wirelessly transmit data indicative of the collected ECG information for receipt by another system such as a hospital, clinic or home-based monitoring system. In this wearable ECG sensor device example, the device typically includes firstly an adhesive electrode assembly with multiple individual electrodes wherein the assembly is adapted to be attached to the patient's skin, and secondly a sensor assembly that includes all of the sensing, processing and communication electronics and a power supply for a self-contained sensor-transmitter device. In this case, the electrode assembly provides the direct electrical interface and adhesion to the patient's skin as well as a platform to which the sensor assembly connects and is supported.

Another class of skin electrode assemblies are adapted to be connected by an electrical lead (or in other words, a long wire) to a separate monitoring system, and are intended to be used with the patient "tethered" to the monitoring system. In this electrode assembly example, the patient-worn assembly typically includes an electrode assembly with one or more electrodes adapted to be adhered to the patient's skin and an associated connector assembly with an associated number of contacts to the electrodes of the electrode assembly. The connector assembly is adapted such that a monitoring system lead may be connected to it to provide an electrical connection between the one or more electrodes of the electrode assembly and the sensing and processing circuitry of the separate monitoring system.

SUMMARY

This specification describes technologies relating to systems and methods for detecting a configuration for a patient worn sensor assembly. The patient worn sensor assembly is used for detecting, recording, and communicating patient vital signs includes several structural features that can provide increased signal quality, reduction in signal noise, increased patient comfort, increased reliability, and increased adhesion to a patient's skin. The patient worn sensor can track vital sign information such as blood pressure, body temperature, respiratory rate, blood oxygenation, heart rhythm (via ECG), heart rate, blood glucose level, and bio-impedance levels. The sensor can also track and record additional information about patients, including patient movement, activity, and sleep patterns.

In general, one innovative aspect of the subject matter described in this specification can be embodied in a system for detecting configuration for a patient worn sensor assembly that includes a sensor assembly, a patient monitoring device, a storage unit, and a controller. The sensor assembly includes an adapter including a configuration resistor, and a sensor device including an internal reference resistor, an analog-to-digital (ADC) circuit configured to measure a voltage output from a resistive voltage divider formed by the configuration resistor and the internal reference resistor when a reference voltage is applied, and a first communication unit configured to generate sensor device communication data. The patient monitoring device is communicatively coupled to the sensor assembly via the first communication unit of the sensor device, and the patient monitoring device includes a second communication unit configured to receive the sensor device communication data from the first communication unit of the sensor device. The storage unit stores mapping data that includes associated values between the measured voltage output and an adapter assembly identifier. The controller is operably coupled to the storage unit and configured to identify the adapter assembly based on the mapping data and the measured voltage output.

These and other aspects can each optionally include one or more of the following features. The sensor device of the sensor assembly can include the controller and the storage unit, where the sensor device communication data is sent from the sensory assembly to the patient monitoring device includes the identified adapter assembly. The patient monitoring device can include the controller and the storage unit, where the sensor device communication data is sent from the sensory assembly to the patient monitoring device includes the measured voltage output from the resistive voltage divider. The mapping data is associated with a first range of measured voltage outputs indicative of the configuration resistor. The mapping data can include a plurality of ranges of measured voltage outputs, the plurality of ranges of measured voltage outputs includes the first range of measured voltage outputs, and each range of measured voltage outputs is associated with different configuration data for a respective sensor assembly of a plurality of sensor assemblies, where each respective sensor assembly of the plurality of sensor assemblies includes a unique configuration resistor. The sensor assembly can be a particular sensor assembly of the plurality of sensor assemblies, where the patient monitoring device is configured to determine, based on the configuration data, application specific parameters for the particular sensor assembly. The application specific parameters can include a number leads for the particular sensor assembly. The patient monitoring device can further include a display. The application specific parameters can further include graphical display data that specifies graphical contents to be displayed on the display of the patient monitoring device. The application specific parameters can further include a type of harness configuration for the particular sensor assembly.

In general, one innovative aspect of the subject matter described in this specification can be embodied in a method that includes receiving, by a computer system, sensor assembly data for a particular sensor assembly, accessing, by the computer system, sensor assembly identifier information defining a plurality of sensor assembly identifiers, wherein each sensor assembly identifier is associated with a respective sensor assembly, identifying, by the computer system and based on the sensor assembly data, a particular sensor assembly identifier for the particular sensor assembly, and determining, by the computer system, configuration information for the particular sensor assembly based on the particular sensor assembly identifier. Other embodiments of this aspect include corresponding systems, apparatus, and computer programs, configured to perform the actions of the methods, encoded on computer storage devices.

These and other aspects can each optionally include one or more of the following features. The sensor assembly data can include a measured voltage output from a resistive voltage divider formed by a configuration resistor and an internal reference resistor when a reference voltage is applied, where the configuration resistor is unique for each respective sensory assembly. The sensor assembly data can include resistor data specifying a particular resistance. The computer system can be a patient monitoring device. The sensor assembly can be an electrode assembly configured to be applied to the skin of a patient. The configuration information can include a number leads for the particular sensor assembly. The configuration information can include a type of harness configuration for the particular sensor assembly. Determining configuration information for the particular sensor assembly can further include generating, by the computer system, graphical display data that specifies graphical contents for the particular sensor assembly to be displayed on a display of the computer system.

In general, one innovative aspect of the subject matter described in this specification can be embodied in a patient monitoring device for use with a sensor assembly configured to be applied to the skin of a patient that includes a communication unit, a storage unit, and a controller. The communication unit is configured to receive sensor device communication data from a sensor assembly. The storage unit is configured to store sensor assembly identifier information defining a plurality of sensor assembly identifiers, where each sensor assembly identifier is associated with a respective sensor assembly. The controller is operably coupled to the storage unit and configured to receive sensor assembly data for a particular sensor assembly, access, from the storage unit, the sensor assembly identifier information, identify, based on the sensor assembly data, a particular sensor assembly identifier for the particular sensor assembly, and determine configuration information for the particular sensor assembly based on the particular sensor assembly identifier.

These and other aspects can each optionally include one or more of the following features. The sensor assembly data can include a measured voltage output from a resistive voltage divider formed by a configuration resistor and an internal reference resistor when a reference voltage is applied, where the configuration resistor is unique for each respective sensory assembly. The sensor assembly data can include resistor data specifying a particular resistance. The sensor assembly can be an electrode assembly configured to be applied to the skin of a patient. The configuration information can include a number leads for the particular sensor assembly. The configuration information can include a type of harness configuration for the particular sensor assembly. The controller can be further configured to generate graphical display data that specifies graphical contents for the particular sensor assembly to be displayed on a display of the computer system.

In general, one innovative aspect of the subject matter described in this specification can be embodied in a method for identifying a sensor assembly configuration for a sensor assembly configured to be applied to the skin of a patient that includes generating, at a reference pin, a reference voltage, obtaining, at an output pin, an output voltage when a particular adapter of a plurality of adapters is connected to the sensor, where each adapter includes a unique configuration resistor connected to a reference pin and an output pin of the adapter, identifying, by a controller and based on the output voltage, a sensor assembly identifier for the particular adapter, accessing, by the controller, sensor assembly identifier information defining a plurality of sensor assembly identifiers and configuration information for each adapter, wherein each sensor assembly identifier is associated with a respective sensor assembly, and determining, by the controller, configuration information for the particular adapter based on the particular sensor assembly identifier. Other embodiments of this aspect include corresponding systems, apparatus, and computer programs, configured to perform the actions of the methods, encoded on computer storage devices.

These and other aspects can each optionally include one or more of the following features. The sensor assembly can include the sensor and the adapter. The sensor can include the controller. The configuration information can include a number leads for the particular sensor assembly. The configuration information can include a type of harness configuration for the particular sensor assembly. The sensor assembly can be an electrode assembly configured to be applied to the skin of a patient.

In general, one innovative aspect of the subject matter described in this specification can be embodied in a sensor assembly including an adapter including a configuration resistor, and a sensor device including an internal reference resistor, an ADC circuit configured to measure a voltage output from a resistive voltage divider formed by the configuration resistor and the internal reference resistor when a reference voltage is applied when the adapter is connected to the sensor, a storage unit configured to store sensor assembly identifier information defining a plurality of sensor assembly identifiers, wherein each sensor assembly identifier is associated with a respective sensor assembly, and a controller operably coupled to the storage unit and configured to determine, based on the output voltage, a sensor assembly identifier for the particular adapter, access, from the storage unit, the sensor assembly identifier information, and determine configuration information for the particular adapter based on the particular sensor assembly identifier.

These and other aspects can each optionally include one or more of the following features. The sensor assembly can include the sensor and the adapter. The sensor can include the controller. The configuration information can include a number leads for the particular sensor assembly. The configuration information can include a type of harness configuration for the particular sensor assembly. The sensor assembly can be an electrode assembly configured to be applied to the skin of a patient.

Particular embodiments of the subject matter described in this specification can be implemented so as to realize one or more of the following advantages. Utilizing an ADC circuit to automatically detect a configuration for a patient worn sensor assembly to provide a plug-and-play functionality provides several advantages for healthcare practitioners. For example, if the healthcare practitioner desired to replace the current sensor assembly with a sensor assembly having different capabilities (i.e., add a finger sensor to measure oxygen saturation), the system would automatically update with the application specific parameters and the bedside monitor would provide the additional user interface measurement. The healthcare practitioner would benefit from having a system automatically adjust to the type of sensor assembly that the healthcare practitioner connected, as opposed to having to look for the proper configuration settings at the bedside monitor. Thus, the healthcare practitioner can spend more time on patient care and less time having to reconfigure the system if they plug in a new sensor assembly. Additionally, such a system allows portions of a sensor assembly that are consistent across multiple different sensor assembly configurations to be reused with various different sensor assembly arrangements, thereby reducing the amount of equipment that needs to be kept on hand and maintained. Such systems can also reduce the amount of components required for providing various patient monitoring processes over traditional patient monitoring systems while providing increased flexibility for use in numerous patient monitoring scenarios.

In accordance with some aspects described herein, bandwidth usage may be controlled and processor efficiency may be increased by automatically detecting the configuration of the connected sensor assembly and updating the bedside monitor application parameters accordingly. For example, if the sensor assembly needed for a particular application only required a short lead ECG measurement, the system would not continuously be looking to measure body temperature and blood oxygen saturation measurements, or be trying to acquire accelerometer data for patient movement tracking. This can result in more efficient utilization of bandwidth and computing resources.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Described below are systems and methods for automatically identifying application specific parameters and configuration information for a plurality of unique patient worn sensor assemblies. Each sensor assembly includes an adapter with a unique resistor value built in to each unique product configuration. For example, each unique configuration can specify a number of ECG leads, the type(s) of sensors attached to the sensor assembly, mapping of measurements to ECG leads and associated calculations, display content of specific waveforms, arrangement, and grayed out options, and signal processing coefficients. When the adapter of the sensor assembly is electrically coupled to a chest sensor device, the system can automatically obtain the configuration data, and provide the data to a bedside monitor system that is communicatively coupled to the chest sensor device.

In particular, this technology focuses on an analog-to-digital (ADC) circuit at the chest sensor device that measures voltage from a resistive voltage divider formed by a configuration resistor in the adapter and an internal reference resistor at the chest sensor. The ADC circuit captures a voltage value and provides a numerical output that are mapped to indicate a particular configuration. Because of electrical component tolerance and measurement noise, specific configurations are represented by a range of values rather than one specific value. The ADC values can then be packetized and inserted into the protocol data stream for transmission to the bedside monitor. The bedside monitor can then analyze the data stream, and based on the ADC value, determine the specific configuration for the sensor assembly and provide the adequate subsequent action. For example, the bedside monitor can update the graphical user interface (GUI) for the specific sensor assembly attached, provide different protocols for the ECG based on the number leads, and the like. Alternatively, the chest sensor device can analyze the ADC values, and provide the configuration information to the bedside monitor.

These features and additional features are described in more detail below.

Figure 1:
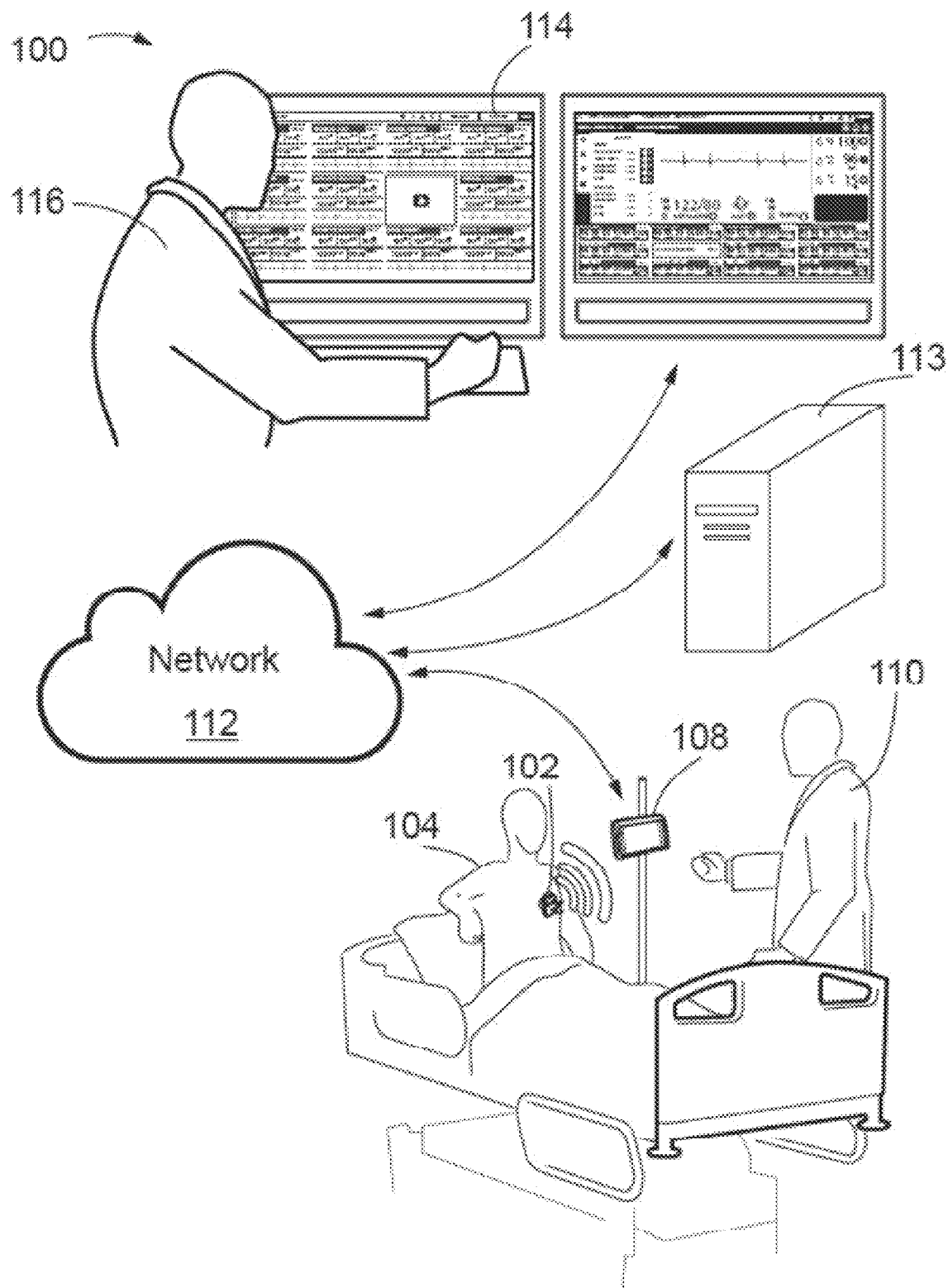
FIG. 1 shows an example system for tracking and monitoring information associated with a patient using a patient worn sensor assembly.

FIG. 1 shows an example system 100 for tracking and monitoring information associated with a patient. The system 100 can be used to monitor patient vital signs, track patient activity, track patient movement, record information associated with a patient, coordinate patient care, and provide up-to-date information to health care providers. The system 100 includes one or more patient worn sensors for detecting and recording various vital signs and other information for a patient. For example, the system 100 can include a chest sensor 102 affixed to the chest of a patient 104 for tracking various vital signs of the patient 104. The system 100 can additionally include patient worn sensors that can interact with other components of the system 100 to identify alarm states for the patient 104. Alarm states can include various medical states or medical emergencies for the patient that may or may not require intervention by one or more caregivers. In some implementations, alarm states can be identified based on deviation of one or more vital signs or other metrics for the patient 104 outside of an acceptable range. Detection of an alarm state or other issue associated with the patient 104 or components of the system 100 that requires attention can result in one or more components of the system issuing an alert. An alert can take the form of information regarding an alarm state or other issue being displayed by a computing device, a notification sent to one or more caregivers, an audio alarm, a visual alarm, a tactile alarm (such as vibration), or another indicator.

The chest sensor 102 can include several adherent electrodes for contacting the skin of the patient 104 to record various vital signs for the patient, including heart rhythm (via ECG) and heart rate. The chest sensor 102 can be, for example, a 6-lead ECG sensor having I, II, III, aVL, aVR, and aVF leads. Other vital signs that can be monitored by the chest sensor 102 can include blood pressure, body temperature, respiratory rate, blood oxygenation, blood glucose level, hydration levels and perspiration. In some implementations, the chest sensor 102 can include a reusable or permanent portion as well as disposable portions. For example, the chest sensor 102 can include a permanent housing for storing electrical components for processing signals received from and detected in association with the patient and for transmitting information to other devices. The chest sensor 102 can further include a disposable adherent electrode pad designed to affix to the chest of the patient 104. Electrodes included as part of the disposable adherent electrode pad are configured to contact electrical leads of the permanent housing to convey signals from the patient 104 to the electrical components within the chest sensor 102. In some implementations, the permanent housing can include snap connectors for engaging electrodes of the disposable adherent electrode pad and for securing the disposable adherent electrode pad to the permanent housing. The disposable adherent electrode pad can be periodically removed and replaced with a fresh disposable adherent electrode pad while allowing many of the components of the chest sensor 102 to be continually reused. In some implementations, the permanent portion of the chest sensor 102 can include two or more releasably coupled components that can be detached and swapped out for other components. For example, the permanent portion of the chest sensor 102 can include a circuit assembly portion that includes processing components and wireless communication components that is configured to couple with a variety of adapter lead assemblies having various different configurations for sensing different sets of patient vital signs.

The chest sensor 102 can also include sensors for detecting bio-impedance in order to monitor hydration levels, body fat levels, or other fluid levels for the patient 104. In some implementations, the chest sensor 102 can include electronics for processing and analyzing vital sign information and other information collected from the patient 104. In some implementations, the chest sensor 102 and/or other patient worn sensors collect raw, pre-processed information which is transmitted to other portions of the system 100 for further processing and analysis.

In some implementations, the chest sensor 102 includes a temperature sensor that extends from a main body of the chest sensor 102 to underneath the patients 104 armpit for monitoring, tracking, and recording body temperature for the patient 104. The temperature sensor can include both reusable portions and temporary/disposable portions. For example, the temperature sensor can include a disposable contact for affixing to the patients 104 skin under the patients 104 armpit. The temperature sensor can, for example, further include permanent portions that include temperature sensing portions, circuitry for interpreting and processing temperature data received from the patient, and a cable running from the main body of the chest sensor 102 around the chest of the patient 104 to the patients 104 armpit. In some implementations, rather than including functionality for interpreting temperature data collected from the patient 104, the temperature sensor can collect raw data that is processed by circuitry contained within the main housing of the chest sensor 102 or other portions of the system 100.

In some implementations, the chest sensor 102 includes one or more accelerometers for detecting and recording patient motion, activity, position, and posture. For example, an accelerometer included within the chest sensor 102 can track patient activity to allow a caregiver to determine if the patient 104 is receiving a sufficient level of daily exercise, or if the patient 104 is engaging in too much activity for the current physical condition of the patient 104. The accelerometer can also be used to determine if the patient 104 has fallen, or if the patient 104 has been motionless for a specified period of time. For example, the accelerometer can determine that the patient has been in a particular posture for more than a specified time period, which can allow the system 100 to identify an alarm state for the patient and send out one or more alerts to elicit a caregiver response to the patient's alarm state. Additionally, or alternatively, the accelerometer is used to track patient sleep patterns, and/or to track the posture of the patient 104 to allow caregivers to provide recommendations for how the patient 104 can better position himself when seated, lying, standing, etc. The accelerometer could additionally provide information to caregivers that is used to determine if the patient 104 is engaging in activities or habits that can increase the risk of re-injury or of developing complications.

The chest sensor 102 can also include circuitry and components for identifying a physical location of the patient 104. For example, the chest sensor 102 can include a GPS unit or a radio signal triangulation based location determination device. Additionally, or alternatively, a GPS unit or other location determination circuitry included within the chest sensor 102 are used, for example, to identify a location of a patient when the patient is not located where the patient should be at a specified time. For example, the GPS unit is used to locate patients suffering from dementia or other mental illnesses who are prone to wandering and becoming lost. As another example, if the accelerometer in the chest sensor 102 determines that the patient 104 has fallen, the chest sensor 102 can transmit an alert to one or more caregivers that includes the location of the patient 104 to allow the caregivers to more easily determine where the patient 104 has fallen and attend to the patient's 104 needs quickly and effectively.

Other components that can be included as part of the chest sensor 102 include a power supply, buttons or other input mechanisms for receiving user input, one or more audible alarms or speakers, and display lights or a display screen. A power supply for the chest sensor 102 can take the form of a battery pack for receiving standard disposable batteries, a rechargeable battery, or a removable battery pack that can be replaced with a fully charged battery pack. The chest sensor 102 can further include input mechanisms such as, for example, buttons, keys, or a touch screen. The input mechanisms can allow the patient 104 or a caregiver to adjust settings for the chest sensor 102, perform various tests (such as sensor tests, battery power level tests, etc.) or reset one or more alarms for the chest sensor 102. For example, the patient 104 or a caregiver can silence an audible alarm of the chest sensor 102 or stop a flashing light alarm of the chest sensor 102 by pressing a button on the chest sensor 102.

The chest sensor 102 can also include one or more audible alarms or speakers. Speakers or other noise emittance units included as part of the chest sensor 102 can provide an audible alarm when a particular patient event occurs. In some instances, different types of audible alarms can indicate different patient events. For example, a first alarm sound can indicate cardiac arrest while a second alarm sound can indicate that the patient 104 has fallen and a third alarm can indicate irregular respiration for the patient 104. In some instances, buttons or other input devices of the chest sensor 102 can be used to pause or reset an audible or visual alarm. The chest sensor 102 can also include display lights, a display screen, or other display mechanisms. For example, one or more LED lights can indicate a current status of one or more vital signs of the patient 104 or a current status of one or more components of the chest sensor 102. For example, an LED can indicate that a battery of the chest sensor 102 is low, while another LED can indicate that a communications unit (e.g., wireless Bluetooth communication circuitry) is malfunctioning. As yet another example, a display screen included as part of the chest sensor 102 can provide indications of one or more vital signs or other information collected by the chest sensor 102. For example, a display screen can show one or more ECG readings for the patient 104.

In some instances, buttons or other input devices of the chest sensor can allow the patient 104 to initiate a patient distress call. For example, the patient 104 can select a button on the chest sensor 102 which can cause the chest sensor 102 to communicate a distress signal to a bedside monitor 108, or to another computing device using wireless communications and/or by communicating through a network 112. For example, when the patient 104 presses the button, the chest sensor 102 can transmit a distress signal to a computer located at a nursing station. The nursing station can then indicate to a caregiver that the patient 104 has initiated a distress call. Additionally, information related to the distress call can be recorded and stored along with an indication of a time when the distress call was made, and vital sign and other information for the patient at the time of the distress call.

In some implementations, one or more input devices of the chest sensor 102 can initiate microphone functionality of the chest sensor 102. For example, the patient 104 can select a button on the chest sensor 102 to activate a microphone included in the chest sensor 102. The microphone can allow the patient 104 to make an audio recording, for example, to indicate symptoms currently being experienced, or recently experienced by the patient 104. Additionally, or alternatively, the audio recording is recorded along with a time stamp of when the recording was made and stored in computer memory of the chest sensor 102 and/or another computing device in communication with the chest sensor 102. The audio recording (e.g., that includes the patient 104 reciting symptoms) can be used by one or more caregivers in diagnosing the patient 104.

In some implementations, the microphone functionality of the chest sensor 102 is used to facilitate one-way or two-way audio communication between the patient 102 and a caregiver located at a different location. For example, the patient 104 can select a button of the chest sensor 102 to activate the microphone of the chest sensor 102 and initiate a two-way audio communication session with a caregiver located at a computing device at a different physical location than the patient 104 and the chest sensor 102. For example, the patient 104 can talk to a nurse located at a nursing station on the same floor of a hospital as the patient 104 to communicate problems, symptoms, or other information to the nurse. The nurse can communicate back to the patient 104. For example, the chest sensor 102 can include a speaker to emit audio transmitted by the nursing station to allow the nurse to provide instructions or comfort to the patient 104, or to inform the patient 104 that help is on the way.

As mentioned above, patient worn sensors included as part of the system 100 can include a wrist sensor, a finger sensor, an ear sensor, or the like. Each sensor can be used to track and record blood pressure and blood oxygenation (SpO2) for the patient 104. As with the chest sensor 102, each sensor can include both reusable and disposable portions. For example, each sensor can include a reusable housing and circuitry for processing signals received from the patient 104 and a disposable portion for contacting the skin of the patient 104. In some implementations, the wrist sensor includes a finger sensor that extends from the wrist sensor and engages one or more fingers of the patient 104. Finger sensor 402 is further described herein with reference to FIGS. 4A-4B. A finger sensor is used, for example, to measure blood oxygenation (SpO2) for the patient 104. In some implementations, rather than being located at the wrist of the patient 104, the wrist sensor can take the form of an upper arm sensor that is located at the upper arm (above the elbow) of the patient 104. The upper arm sensor is used, for example, to measure blood pressure for the patient 104. Additionally, or alternatively, an ear sensor is used to measure blood oxygenation (SpO2) for the patient 104. Ear sensor 502 is further described herein with reference to FIG. 5.

The chest sensor 102 can communicate with a bedside monitor 108 to convey information collected by the chest sensor 102 and/or other patient worn sensors (e.g., patient vital signs, patient activity, and patient location) to the bedside monitor 108. For example, the chest sensor 102 can wirelessly communicate with the bedside monitor 108 and other patient worn sensors using Bluetooth technology. As another example, the chest sensor 102 can communicate with the bedside monitor 108 using a WiFi protocol or a cellular protocol. As yet another example, the chest sensor 102 can use a wired connection to communicate with the bedside monitor 108. Additionally, or alternatively, the chest sensor 102 is connected to an adapter to form a sensor assembly. The sensor assembly including the chest sensor connected to an adapter is further described herein with reference to FIGS. 2-9.

In some implementations, the communication connection between the chest sensor 102 and bedside monitor 108 can also be used to relay information from the bedside monitor 108 to the chest sensor 102. For example, the bedside monitor 108 is used to change settings for the chest sensor 102, such as acceptable ranges for heart rate, respiratory rate, blood oxygenation, or other vital signs monitored by the chest sensor 102 and/or other patient worn sensors. As another example, the bedside monitor 108 is used to change a frequency at which particular vital signs for the patient 104 are captured and transmitted by the chest sensor 102. As yet another example, the bedside monitor 108 is used to change a sensitivity level of one or more vital sign reading components of the chest sensor 102 and/or other sensors connected to the sensor assembly.

The bedside monitor 108 can allow a caregiver 110 (e.g., a nurse, doctor, orderly, physical therapist, or other caregiver) to view real-time vital signs for the patient 104, past vital signs for the patient 104, other information provided by the chest sensor 102, and/or other patient worn sensors, or other information associated with the patient 104. For example, the bedside monitor 108 can display an ECG waveform for the patient 104 while also listing a current blood oxygenation level, blood pressure, hydration level, heart rate, respiration rate, and body temperature for the patient 104. The caregiver 110 can also use the bedside monitor 108 to make notes regarding patient care for the patient 104, make annotations for vital sign information or other patient information, send messages to other caregivers, or log patient activities. For example, the caregiver 110 can use the bedside monitor 108 to make a note that the patient 104 has experienced mild trouble breathing, or that the patient 104 is experiencing limb pain. As another example, the caregiver 110 may be a physical therapist and can use the bedside monitor 108 to log a therapy activity for the patient 104 and make notes about physical therapy progress for the patient 104. As yet another example, the caregiver 110 can use the bedside monitor 108 to adjust ranges for what is considered a "normal" or "safe" range for one or more vital signs for the patient 104. As yet another example, the caregiver 110 may be a hospital orderly and can use the bedside monitor 108 to record when the patient 104 has eaten meals, and how much the patient 104 has eaten at each meal.

The bedside monitor 108 can also be used to review notes on patient care for the patient 104 left by other caregivers, or track patient vital signs and activity for a period of time in order to assist in diagnosis or prevention of complications. The bedside monitor 108 can also convey information associated with alarm states for the chest sensor 102. For example, if any of the various vital signs or other information (such as patient motion/location) falls outside of specified "safe" limits, the chest sensor 102, other sensors, or bedside monitor 108 can initiate an alarm state. The bedside monitor 108 can alert the caregiver 110 to the alarm state through use of visual or audio alarms. In some scenarios, different visual or audio alarms can be used for distinct types of alarm states, or for varying emergency levels associated with different alarm states.

In addition to communicating with the chest sensor 102, and/or other patient worn sensors, the bedside monitor 108 can also communicate with one or more central servers 113 through a network 112. The central server 113 can collect information provided by the bedside monitor 108, other bedside monitors, various sensors, and other computing terminals. The central server 113 can include multiple servers that are co-located, or multiple servers located at distinct geographic locations to provide so called "cloud" storage for information stored by the system 100. The one or more central servers 113 can be accessed through the network 112 from many different locations by various devices, including the bedside monitor 108, other bedside monitors and computing devices located at the same hospital as the bedside monitor 108, and various bedside monitors and other computing devices (e.g., mobile phones, personal computers, tablet devices, etc.) located at other physical locations.

Information collected by the central server 113 is accessed at a central server station 114. For example, a caregiver 116 or other hospital personnel can use the central server station 114 to access information for the patient 104, other patients, or other hospital or healthcare administrative functions. The network 112 can be an intra-hospital local area network (LAN) such as a WiFi network, a wide area network (WAN) such as the Internet, or any combination of LAN and WAN networks. The bedside monitor 108 can connect to the network 112 using a wireless protocol such as WiFi or a cellular communication protocol, or through a wired connection. In some implementations, the central server station 114 may be located at a distinct facility from the patient 104 and bedside monitor 108.

The central server station 114 can allow the caregiver 116 to monitor vital signs, activities, and other information for the patient 104 from a remote location. The central server station 114 can additionally allow the caregiver 116 to observe information for multiple patients within a healthcare facility or system simultaneously. In some implementations, all information collected by the patient worn sensors (e.g., the chest sensor 102) and all information entered using the bedside monitor 108 is stored by the central server 113 and is accessible through the central server station 114. In some implementations, the caregiver 116 can receive alarms or alerts associated with the patient 104 at the central server station 114 and take appropriate actions to dispatch one or more caregivers to address the alarm situation. In some implementations, the system 100 can automatically recognize an alarm state for the patient 104 and alert an appropriate caregiver to respond to the situation. For example, the bedside monitor 108 can analyze information received from the chest sensor 102 to determine that the patient 104 is choking. The bedside monitor 108 can recognize this as an emergency level alert, and transmit this information to the central server 113. The central server 113 can identify one or more caregivers within close proximity to the patient 104 and alert them that the patient 104 is choking.

The alerts can be sent to the one or more caregivers, for example, through bedside monitors with which the caregivers are currently interacting, computer terminals in communication with the central server 113, mobile devices carried or worn by the caregivers, or alarms or displays located throughout a hospital or healthcare facility where the patient 104 is located. The central server 113 can also transmit alert information regarding the patient 104 to the central server station 114 to notify the caregiver 116 as well as the beside monitor 108 (which is associated with the chest sensor 102 worn by the patient 104) to alert the caregiver 110 or perhaps one or more other caregivers in the vicinity of the bedside monitor 108. This automated recognition of an alarm state for the patient 104 and routing of the alarm to caregivers within close proximity to the patient 104 can reduce the time taken to respond to and resolve the emergency, which, in turn, reduces adverse effects for the patient 104.

In some implementations, in addition to information collected by the various patient worn sensors (such as the chest sensor 102, and/or other patient worn sensors) the bedside monitor 108 can include functionality for collecting information related to the patient 104. For example, the bedside monitor 108 can include one or more cameras for monitoring movements, posture, and other aspects of the patient 104. For example, the cameras can be built in to the bedside monitor 108, attached to the bedside monitor 108 as peripheral devices, or separate devices in wired or wireless communication with the bedside monitor 108. A camera of the bedside monitor 108 is positioned to face the patient 104 while the patient 104 is located in the bed and monitor movements of the patient 104. This information is used to recognize alarm states for the patient. For example, the bedside monitor 108 (or another computing device of the system 100, such as the central server 113) can analyze video images captured by the camera to identify if the patient 104 has fallen out of the bed. As another example, the camera is used to identify that the patient 104 is not located in the bed at a time when the patient 104 is expected to be located in the bed. If the bedside monitor 108 detects that the patient 104 has been out of bed for longer than a threshold period of time, the bedside monitor 108 can recognize this as an alarm state and alert a caregiver to the situation.

The camera of the bedside monitor 108 can also be used identify one or more dangerous or undesirable conditions for the patient 104. For example, the bedside monitor 108 can use the camera to identify that a guardrail for the patients 104 bed is down (e.g., a caregiver forgot to put the rail back up after assisting the patient 104 into bed). The bedside monitor 108 recognizes this as an alarm state and notifies an appropriate caregiver. As another example, if accelerometer data collected by the chest sensor 102 indicates that the patient 104 has fallen out of bed, the camera of the bedside monitor 108 is used to verify that the patient 104 has fallen out of bed. In some cases, the camera of the bedside monitor 108 can provide a video feed to one or more caregivers (e.g., to a nurse positioned at a nursing station in the same ward as the patient 104) to allow the caregivers to periodically check in on the patient 104 without having to physically enter the patients 104 room.

Other information that can be collected by one or more sensors or devices built into or in communication with the bedside monitor 108 can include environmental temperature, environmental humidity, noise level, light level, carbon monoxide detection, or smoke detection. For example, the bedside monitor 108 can identify that environmental temperature near the patient 104 has fallen below an acceptable level and alert a caregiver or maintenance worker to the change in temperature. As another example, the bedside monitor 108 can detect that environmental humidity has dropped below a threshold value.

In some implementations of the system 100, the chest sensor 102, and/or other patient worn sensors can obviate the need for the bedside monitor 108 by connecting directly to the network 112 (e.g., using a WiFi or other wireless protocol) to transfer vital sign and other information to the central server 113. The information transferred to the central server 113 through the network can be accessed at the central server station 114 and other terminals connected to the network 112. In some implementations, the bedside monitor 108 serves as a dummy terminal that receives information from the central server 113 and displays a graphical user interface dictated by the central server 113 rather than receiving information directly from the chest sensor 102 and/or other patient worn sensors.

In some implementations, information for the patient 104 (such as vital signs, alarm states, treatment information, biographical information, etc.) is accessed using other devices in communication with the central server 113 and/or bedside monitor 108. For example, patient information can be sent to a mobile device (such as a smart phone, tablet or laptop) owned by the caregiver 110 or another caregiver associated with the patient 104. As another example, the caregiver 110 can access the central server 113 (e.g., by using the bedside monitor 108 or another computing device) and indicate that the caregiver 110 wishes to receive updates for the patient 104. Additionally, or alternatively, the caregiver 110 is associated with the patient 104 (for example, by linking a caregiver profile for the caregiver 110 to a patient profile for the patient 104). When important information regarding the patient 104 (such as alarm states, or significant changes in treatment plans) are received by the central server 113, the central server 113 can automatically send this information to a device associated with the caregiver 110, such as the caregivers 110 mobile phone.

In some implementations, a caregiver associated with the patient 104 can use a computing device to communicate with the central server 113 and access information for the patient 104. For example, a caregiver can access information for the patient 104 if the caregiver has proper permission to access the information. The caregiver can indicate permission to access the information by entering an access code, or by accessing a profile for the caregiver that has previously been associated with a patient profile for the patient 104. In some implementations, information associated with the patient 104 is accessed from a number of different bedside monitors or central server stations. Such an information access scheme can allow caregivers and other users of the system 100 to access information for multiple patients. For example, a doctor can be in charge of monitoring the status of a number of patients. The doctor can use a PC to access the central server 113 and view vital sign information, alert information, and other information for each of the multiple patients. Additionally, or alternatively, the information for the multiple patients is arranged in a news feed that allows the doctor to easily access and review the most pertinent patient information, while also providing the ability for the doctor to access additional information for each patient that is not identified by the system 100 as being the most relevant.

The caregiver 110 can additionally use the bedside monitor 108 to access information associated with the patient 104 that has been entered into the system 100 but not provided by the chest sensor 102 or other patient worn sensors. For example, the caregiver 110 can use the bedside monitor 108 to access information associated with the patient 104 regarding treatment or procedures that occurred at locations other than the current location of the patient 104. In one example, the caregiver 110 can use the bedside monitor 108 to access and review information stored at the central server 113 regarding interactions between the patient 104 and emergency room staff to assess a present status for the patient 104. As another example, the caregiver 110 can review notes left by an anesthesiologist at a different bedside monitor for the patient 104 regarding specific vital signs or other behavior for the patient 104 to observe during a specified post-surgical procedure period for the patient 104.

In some implementations, the central server 113 can interface with computing systems outside of the system 100 to access additional information for the patient 104. For example, the central server 113 can access electronic medical records (EMRs), electronic health records (EHRs), or picture archiving and communication system (PACS) information for the patient 104 containing healthcare information for the patient regarding past treatment, procedures, care plans, diagnoses or other healthcare related information for the patient 104 which may or may not be associated with a healthcare facility associated with the system 100.

In some implementations of the system 100, multiple patient worn sensors are associated with multiple respective patients and each of the patient worn sensors is configured to sync with one or more bedside monitors or intermediary devices (e.g., using Bluetooth or another wireless communication protocol). In some implementations, the patient worn sensors can communicate with bedside monitors or other devices using wired connections. In some implementations, some or all of the patient worn sensors are configured to communicate directly with the network 112 (e.g., using Wi-Fi or another wireless communication protocol). Additionally, or alternatively, information collected by the multiple patient worn sensors is routed through the network to the central server 113 and stored. The information is accessed by components of the system 100. For example, the caregiver 116 can access information collected by the multiple patient worn sensors at the central server station 114 to monitor statuses of the patients associated with the multiple patient worn sensors.

In use, one or more patient worn sensors (such as the chest sensor 102) can be associated with the patient 104 upon admittance of the patient 104 to a healthcare facility, or shortly after admittance of the patient 104 to the healthcare facility. In some implementations, if the patient 104 has entered the healthcare facility during an emergency situation (e.g., cardiac arrest, severe car accident, etc.) the patient worn sensors can be issued to the patient 104 after the emergency situation has been addressed and the patient 104 has been stabilized. In some implementations, the patient 104 can be associated with a unique patient identifier ("ID"). The patient ID can be as simple as the patients 104 name, a unique number assigned to the patient 104, a unique combination of numbers, letters, and other characters, or any other unique identifier associated with the patient 104. If the patient 104 has previously interacted with the healthcare facility, the system 100, or a related system, the caregiver 110 can look up the unique identifier for the patient 104 by, for example, entering the patients 104 name at the bedside monitor 108. The caregiver 110 can access patient information for the patient 104. Patient information can include biographical information such as name, age, weight, height, address, contact information, family members, emergency contacts, etc. as well as healthcare information regarding past (or present or future) healthcare events, treatments, procedures, care plans, etc. for the patient 104. In some implementations, the caregiver 110 can access a patient profile for the patient 104 (for example, using the patient ID for the patient 104). The patient profile can include any of the above listed information for the patient 104. The patient profile can also indicate caregivers associated with the patient 104, such as doctors who have performed surgery on the patient 104, doctors scheduled to perform future procedures on the patient 104, one or more caregivers responsible for the primary care of the patient 104, emergency room doctors and attendants who handled initial emergency care for the patient 104, and other caregivers associated with the patient 104.

If the patient 104 has not previously interacted with system 100 or a related system, a new unique ID can be assigned to the patient 104 by one or more components of the system 100 (for example, by the bedside monitor 108 or the central server 113.) Biographical, healthcare, and other information for the patient 104 is entered (e.g., using the bedside monitor 108 or central server station 114) and stored at the central server 113.

When the patient worn monitors (such as the chest sensor 102) are initially provided to the patient 104, the patient worn sensors can be associated with the patient 104 by associating the patient worn sensors with the unique ID for the patient 104. For example, the chest sensor 102 can be synced with the bedside monitor 108. The caregiver 110 can use the bedside monitor 108 to associate the chest sensor 102 with the patient 104. After the chest sensor 102 is associated with the patient 104, the chest sensor 102 can identify the patient 104 to other components of the system 100, such as other bedside monitors, or other monitor stations.

The bedside monitor 108 can sync with the chest sensor 102, for example, by searching for devices within a specified distance of the bedside monitor 108, displaying a list of nearby devices (such as the chest sensor 102, and one or more other patient worn sensors worn by other nearby patients), and allowing the caregiver 110 to select the chest sensor 102 from the list of displayed devices. After syncing, the caregiver 110 can associate the chest sensor 102 with the patients 104 unique patient ID. As another example, the caregiver 110 can sync the bedside monitor 108 with the chest sensor 102 by entering a unique sensor ID for the chest sensor 102 at the bedside monitor 108. The unique sensor ID can be, for example, printed on the surface of the chest sensor 102. In some implementations, the bedside monitor 108 is synced with the chest sensor 102 using a special scanning device in communication with the bedside monitor 108. The caregiver 110 can use the scanning device to scan the chest sensor 102 (e.g., by detecting a signal being transmitted by a component of the chest sensor 102, scanning an RF ID tag, or by reading a barcode printed on the chest sensor 102). The bedside monitor 108 can use information from the scanning device to identify the chest sensor 102 and sync with the chest sensor 102. In some implementations, the bedside monitor 108 can include a scanning device that is incorporated into the design of the bedside monitor 108. For example, the bedside monitor can be a tablet device that has one or more built in cameras that can be used to scan the chest sensor 102.

In an exemplary implementation, a chest sensor can connect to an adapter lead assembly to create a sensor assembly. The chest sensor 102 and/or bed side monitor 108 can automatically determine configuration information of the sensor assembly (e.g., a number leads, the types of measurement capabilities, graphical display information, etc.) based on a configuration interpretation of the adapter. The sensor assembly and the process for determining configuration information for an adapter connected to the chest sensor is further described below with reference to FIGS. 2-9.

Figure 2:
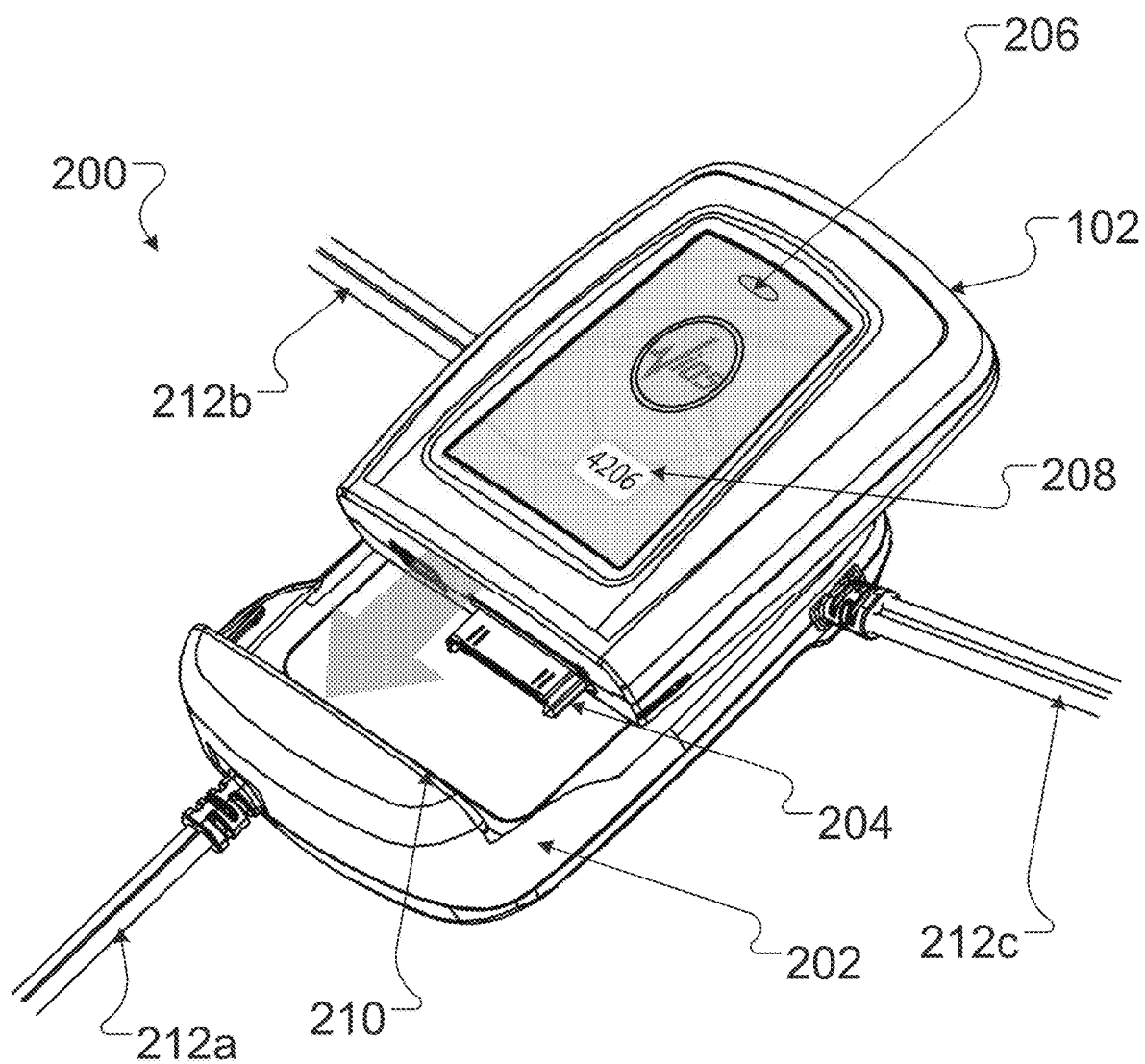
FIG. 2 shows an example perspective view of a patient worn sensor assembly.

FIG. 2 shows an example perspective view of a sensor assembly 200. In particular, FIG. 2 illustrates a chest sensor 102 connecting to an adapter lead assembly 202 in the direction of the arrow as shown. In the example depicted in FIG. 2, the chest sensor 102 includes a male 30-pin connector 204 that is configured to connect to a female 30-pin connector 210 of the adapter lead assembly 202. In various other implementations, the connectors 204 and 210 can be, for example, corresponding USB connectors, firewire connectors, lightening connectors, 30-pin connectors (such as, for example, a JAE 30 pin DD1 series connector), a custom proprietary connector, or any suitable connector that would be known to a person having ordinary skill in the art.

In some implementations, the adapter lead assembly 202 includes lead wires 212a, 212b, and 212c (generally referred to herein as lead wires 212). The adapter lead assembly 202 can include several different unique configurations as a plug-and-play device. For example, the adapter lead assembly 202 can be one of a short lead, a long lead, or a harness assembly. Additionally, each of the adapter lead assembly 202 can include a different type of sensor. For example, the adapter lead assembly 202 could include a finger sensor to measure oxygen saturation. Alternatively, the adapter lead assembly 202 could include an ear sensor oximeter to measure oxygen saturation. Additionally, the adapter lead assembly 202 can include at least one or more of the following vital sign measurement capabilities: ECG, temperature, oxygen saturation, blood pressure, or any other vital sign measurement discussed herein. For example, one adapter lead assembly 202 configuration could be a long lead with ECG and oximeter measurement sensing capabilities. As another example, an adapter lead assembly 202 configuration could be a harness with only ECG measurement sensing capabilities. Additionally, or alternatively, any number of combinations of measurement capabilities and lead wire assemblies are created as needed, including any combination of the above described sensors.

In some implementations, the sensor 102 can also include display lights, a display screen, or other display mechanisms. As shown, sensor 102 includes an indicator 206 and a display screen 208. For example, indicator 206 can include one or more light emitting diode (LED) lights that can indicate a current status of one or more vital signs of a patient wearing the patient worn sensor 102 or a current status of one or more components of the patient worn sensor 102. For example, indicator 206 can indicate to a user, such as a nurse, that the chest sensor 102 was successfully connected to the adapter lead assembly 202. For example, the indicator 206 would show a "green" light if the patient worn sensor 102 was successfully connected to the adapter lead assembly 202. Additionally, or alternatively, if the chest sensor 102 was not successfully connected, the indicator 206 would show a "red" light. As shown, indicator 206 is a LED, however, a similar light emitting component may be used. Additionally, or alternatively, indicator 206 can indicate that a battery of the patient worn sensor 102 is low, while another LED can indicate that a communications unit (e.g., wireless Bluetooth communication circuitry) is malfunctioning. In some implementations, the indicator 206 can illuminate in a variety of colors or flash at varying rates to convey information. In some implementations, the sensor housing can include a display screen 208 to provide indications of settings of the patient worn sensor 102 or vital sign information or other information collected by the patient worn sensor 102. For example, a display screen 208 can show one or more ECG readings for a patient. In some implementations, display screen 208 can show a serial number of the chest sensor 102.

Figure 3A:
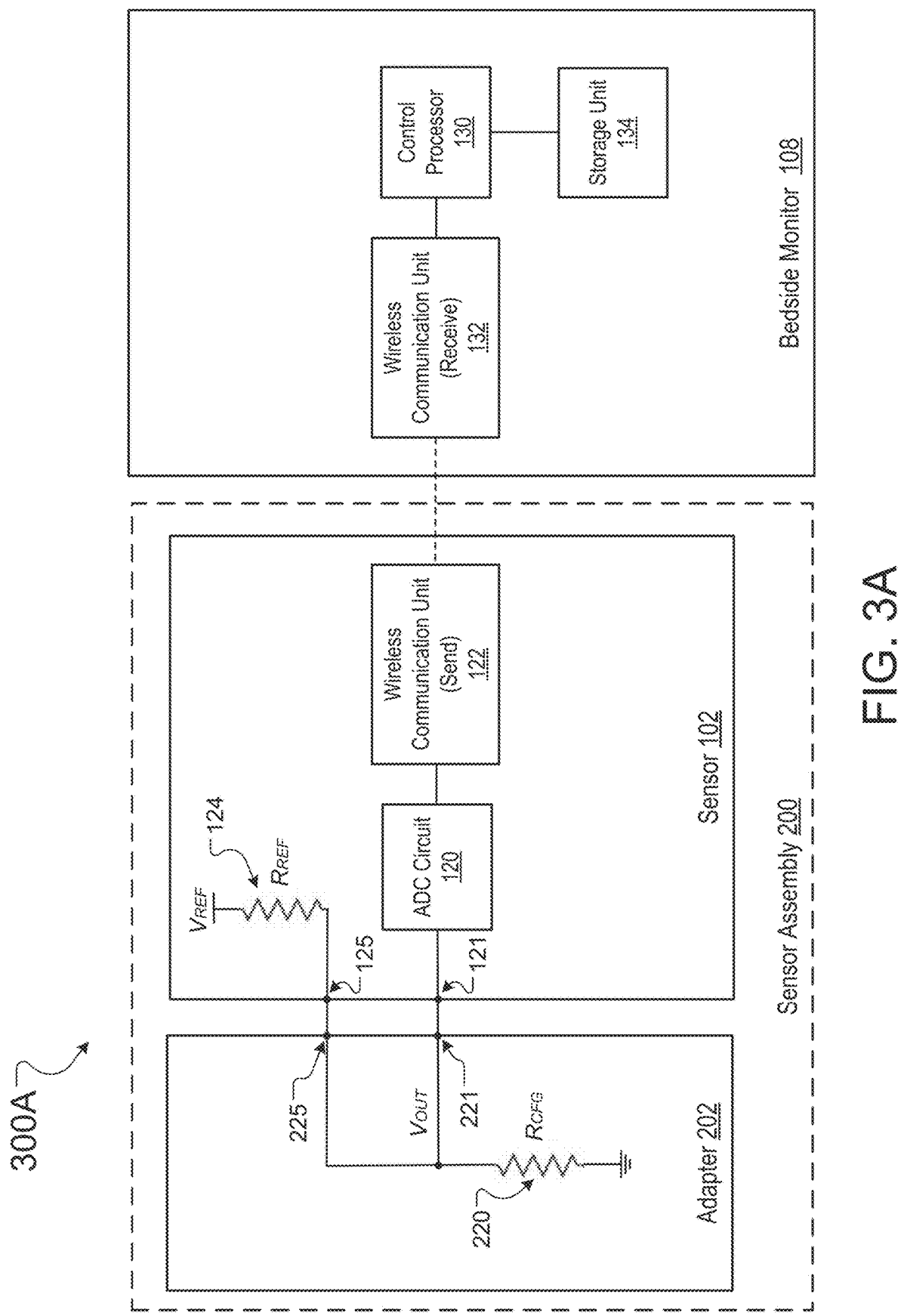
FIG. 3A-3B are block diagrams of an example patient worn sensor assembly in communication with a bedside monitor.
Figure 3B:
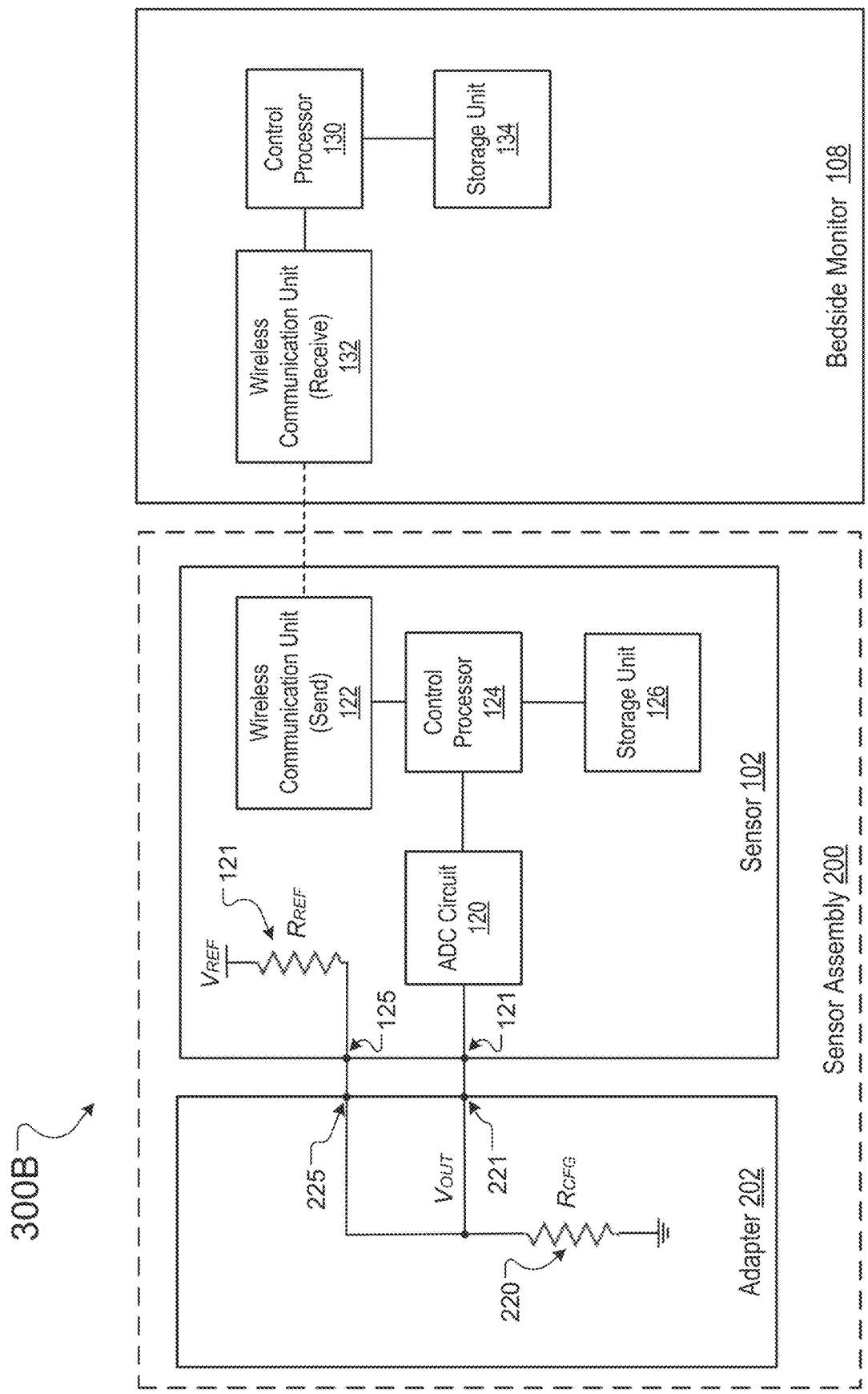

FIG. 3A-3B are block diagrams of an example patient worn sensor assembly in communication with a bedside monitor. In particular, FIG. 3A shows environment 300A with a sensor assembly 200 in communication with a bedside monitor 108, where the bedside monitor 108 determines configuration information for the sensor assembly 200.

The chest sensor 102 includes an analog-to-digital converter (ADC) circuit 120 to measure an output voltage, and a wireless communication unit 122 to communicate with the bedside monitor 108. The chest sensor 102 is configured to send a reference voltage through a reference resistor 124 at pin 125 and receive an output voltage at pin 121.

The adapter lead assembly 202 includes a connector 210 configured to receive a reference voltage at pin 225 and provide an output voltage at pin 221. The adapter lead assembly 202 also includes a configuration resistor 220. The configuration resistor 220 is a unique resistance value assigned to a different type of adapter lead assembly 202 of a plurality of lead assemblies that can be configured to connect to the chest sensor 102. For example, a short lead ECG only adapter lead assembly 202 could be assigned a specific value for the configuration resistor 220, such as 20 k ohms with a resistance precision +/−0.1%. Additionally, a configuration resistor 220 at 10 k ohms with a resistance precision +/−0.1% could be selected for an ECG only long lead adapter configuration. In another example, a configuration resistor 220 at 30 k ohms with a resistance precision +/−0.1% could be selected for a harness adapter configuration with temperature and an oximeter. Each different adapter lead assembly 202 configuration would be provided with a unique configuration resistor 220 such that the system and processes described herein can automatically update the configuration settings (e.g., different screens on the user interface of the bedside monitor 108), when the system detects a different configuration resistor 220 from the ADC circuit 120 conversion. Alternatively, the resistance precision of the configuration resistor 220 can range from 1% to 5%, where, the greater the percentage, the larger ranges of ADC values that could be calculated and the less number of different configurations could be assigned.

The bedside monitor 108 includes a wireless communication unit 132 configured to communicate with the chest sensor 102. The bedside monitor 108 further includes a control processor 130 and a storage unit 134. The control processor 130 is configured to process the received data from the sensor assembly 200, such as the ADC measured values, and determine the application specific parameters for the particular adapter lead assembly 202 that is connected to the chest sensor by accessing a database, such as storage unit 134. The storage unit 134 is configured to store mapping data that includes a range of associated values between the ADC measured values and an adapter assembly identifier. Each adapter assembly identifier is specific to the different configurations of the adapter lead assembly 202 that can be electrically coupled to the chest sensor 102 to form the sensor assembly 200. Each measured ADC value is a converted analog signal to a digital, or numeric signal. For example, a measured ADC value between 10 (low) and 19 (high), may be used for particular configuration, such as a short lead ECG with temperature sensor. As another example, a measured ADC value between 50 (low) and 59 (high), may be used for a different particular configuration, such as a long lead sensor with a temperature sensor and a finger sensor configured as an oximeter sensor.

In operation, a reference voltage can be sent from the chest sensor 102 to the adapter lead assembly 202, and an output voltage can be sent from the adapter lead assembly 202 to the chest sensor 102, when the adapter lead assembly 202 is connected to the chest sensor 102. For example, as shown in FIG. 2, an electrical connection can occur when the male 30-pin connector 204 of the adapter lead assembly 202 is inserted into the female 30-pin connector 210 of the chest sensor 102. In other embodiments, other types of connectors can be used other than 30-pin connectors, as described above. The ADC circuit 120 measures the output voltage from a resistive voltage divider formed by the configuration resistor 220 and the internal reference resistor 124. Because this is an analog measurement, component tolerance and measurement noise can cause specific configurations to be represented by a range of values rather than one value. The specific configuration can be set by case ranges, where each range defines application specific parameters. For example, the configuration and reference resistors used could be in the range of a ±0.1% tolerance level. The ADC circuit 120 may be a 12-bit ADC which results in 4,096 counts. The ADC circuit 120 converts input voltages from $-V_{REF}$ to $+V_{REF}$. For example, $+V_{REF}/2$ ADC input provides a digital output of +1024. The ADC measurement noise can be assumed to be +/−4 counts (i.e., 2 bits). Thus, the range for ADC low to ADC high is 8 counts. For example, a measured ADC value between 153 (low) and 161 (high), may be used for particular configuration, such as harness with ECG only.

After the ADC value is determined, the ADC value can be inserted into a protocol data stream, and the range of values measured by the ADC circuit 120 can be analyzed. In some implementations, the ADC values can be inserted into a protocol data stream transmission and packetized by the communication unit 122 of the chest sensor 102 and sent to the wireless communication unit 132 of the bedside monitor 108. In some implementations, as further described below with reference to FIG. 3B, the chest sensor 102 can determine the configuration information before sending the data to the bedside monitor 108.

In some implementations, if a connection from the chest sensor 102 to the adapter lead assembly 202 is not properly made, or if there is no adapter lead assembly 202 connected, the output voltage would be null. For example, a maximum ADC value (e.g., >1500) is interpreted as a disconnected sensor. In some implementations, a timed sensor shutdown can be initiated when a disconnected sensor is determined. In some implementations, a technical alarm can also be initiated. In some implementations, reconnecting the adapter lead assembly 202 can stop and reset shutdown process.

FIG. 3B shows an example environment 300B with a sensor assembly 200 in communication with a bedside monitor 108, where the chest sensor 102 determines configuration information for the sensor assembly 200 before sending data to the bedside monitor 108.

The chest sensor 102 includes an analog-to-digital converter (ADC) circuit 120 to measure an output voltage, and a wireless communication unit 122 to communicate with the bedside monitor 108. The chest sensor 102 is configured to send a reference voltage through a reference resistor 124 at pin 125 and receive an output voltage at pin 121. The chest sensor 102 further includes a control processor 124 and a storage unit 126. The control processor 130 is configured to process the data from the ADC circuit 120, such as the ADC measured values, and determine the configuration for the particular adapter lead assembly 202 that is connected to the chest sensor. The control processor 124 can determine the configuration by accessing a database, such as storage unit 126. The storage unit 126 is configured to store mapping data that includes a range of associated values between the ADC measured values and an adapter assembly identifier. Each adapter assembly identifier is specific to the different configurations of the adapter lead assembly 202 that can be electrically coupled to the chest sensor 102 to form the sensor assembly 200. Each measured ADC value is a converted analog signal to a digital, or numeric signal. For example, a measured ADC value between 10 (low) and 19 (high), may be used for particular configuration, such as a short lead ECG with temperature sensor. As another example, a measured ADC value between 50 (low) and 59 (high), may be used for a different particular configuration, such as a long lead sensor with a temperature sensor and a finger sensor configured as an oximeter sensor.

One advantage of having the chest sensor 102 determining the adapter assembly identifier is that so the sensor assembly 200 may communicate with another device and provide the application specific parameters, without having to rely on bedside monitor 108 to analyze the measure ADC values. For example, if the bedside monitor is unavailable, a mobile device may be used to acquire the patient vital signs, and the mobile device application may need the application specific parameters to proceed.

Similar to the example environment 300A in FIG. 3A, the adapter lead assembly 202 for the example environment 300B includes a configuration resistor 220 and a connector 210. The bedside monitor 108 includes a wireless communication unit 132 configured to communicate with the chest sensor 102, a control processor 130, and a storage unit 134. However, since the control processor 124 of the chest sensor 102 is determining the configuration of the particular adapter lead assembly, the control processor 130 and the storage unit 134 of the bedside monitor 108 can be used for other operations. For example, the control processor 130 can receive the configuration information, and generate graphical display data that specifies specific graphical contents for the particular sensor assembly to be displayed on a display of the bedside monitor. For example, a particular sensor assembly may provide a particular display, as further discussed herein with reference to user interfaces shown in FIG. 7A-7C.

Figure 4A:
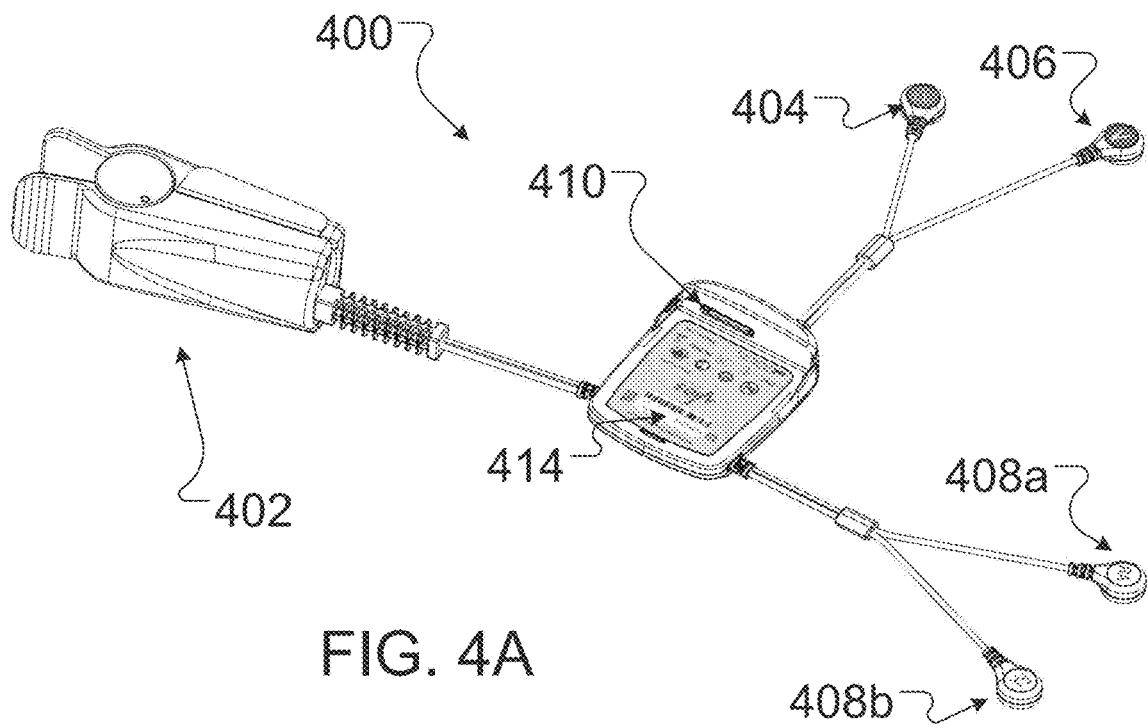
FIGS. 4A-4B show example embodiments of a patient worn sensor assembly.
Figure 4B:
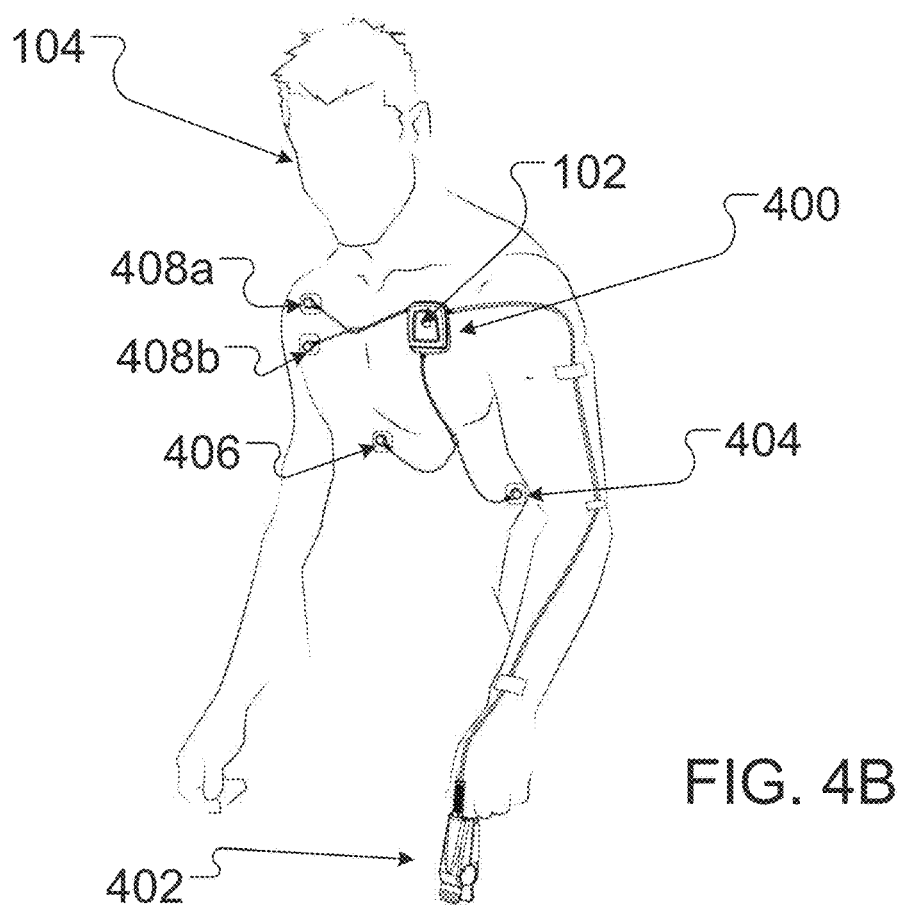

FIGS. 4A and 4B show example embodiments of a patient worn sensor assembly with a finger sensor 402. In particular, FIG. 4A is a perspective view of an adapter lead assembly 400 without a chest sensor attached. The adapter lead assembly 400 can form a portion of an alternative embodiment of the patient worn sensor assembly 200 when coupled with a chest sensor 102 described with respect to FIGS. 1, 2, 3A, and 3B. For example, the adapter lead assembly 400 can be configured to operatively connect to a chest sensor 102 through the connector 410. For example, the 30-pin male connector 204 of the chest sensor 102, can connect to a 30-pin female connector 410. In other embodiments, other types of connectors can be used other than 30-pin connectors, as described above. In some implementations, the adapter lead assembly 400 can be configured to be disposable and replaced by another electrode assembly having an identical or similar design to that of the adapter lead assembly 400, or replaced by an electrode assembly having a different design than the adapter lead assembly 400, such as the adapter lead assembly 500 described below. In some implementations, the adapter lead assembly 400 is reusable and is configured to operatively connect with one or more disposable electrode pads that are configured to affix to a patient's skin.

The adapter lead assembly 400 includes electrode leads 404, 406, 408A, and 408B, and a finger sensor 402. The finger sensor is configured to measure SpO2 and pulse rate, vitals derived from pulse oximetry. The electrode leads 404, 406, 408A, and 408B can be configured to provide a multi-lead ECG. Each electrode lead includes connectors configured to operatively connect with electrode pads. For example, each of the electrode connectors can operatively connect with single electrode pads (for example, "red dot" ECG electrodes) that include electrodes having hydrogels for contacting a patient's skin and collecting vital signs and adhesive layers for securely affixing to the patient's skin. In some implementations, the two electrode connectors are positioned on the right side of a patient to collect vital sign information. The electrode leads 404, 406, 408A, and 408B for the adapter lead assembly 400 include electrically conductive material (e.g., one or more wires) that convey electrical signals from the electrode connectors to the main body (and eventually to a sensor, such as the sensor 102 of FIGS. 1-3).

FIG. 4B shows an example of a patient 104 using a patient worn sensor assembly, and in particular, shows adapter lead assembly 400 of FIG. 4A with chest sensor 102 operatively connected, and the finger sensor 402. The adapter lead assembly 400 is shown affixed to a patient 104. The adapter lead assembly 400 is affixed to a left upper chest portion of the patient 104 near the patients 104 heart.

FIG. 4B additionally shows electrode leads 404, 406, 408A, and 408B. For example, electrode leads 408A and 408B are positioned on the right side of the patients 104 chest to serve as "right arm" leads. FIG. 4B further shows the electrode lead 404 positioned on a left side of the patients 104 abdomen to serve as a "left leg" lead, and electrode lead 406 positioned on the center of the patients 104 abdomen near the sternum to serve as a precordial lead. In the example shown, each electrode lead 404, 406, 408A, and 408B are operatively connected to electrode pads. The electrode pads include electrodes for sensing patient vital signs and adhesive layers for affixing to the patients 104 skin.

In some implementations, the finger sensor 402 transfers information to the chest sensor 102 (e.g., through a wireless or wired connection) and the chest sensor 102 transfers information collected by finger sensor 402 to the bedside monitor 108 and transmits settings information and other information indicated by the bedside monitor 108 to the finger sensor 402. In some implementations, the finger sensor 402 also communicates with the bedside monitor 108 (e.g., through a wireless Bluetooth connection, other wireless connection, or through a wired connection).

Figure 5A:
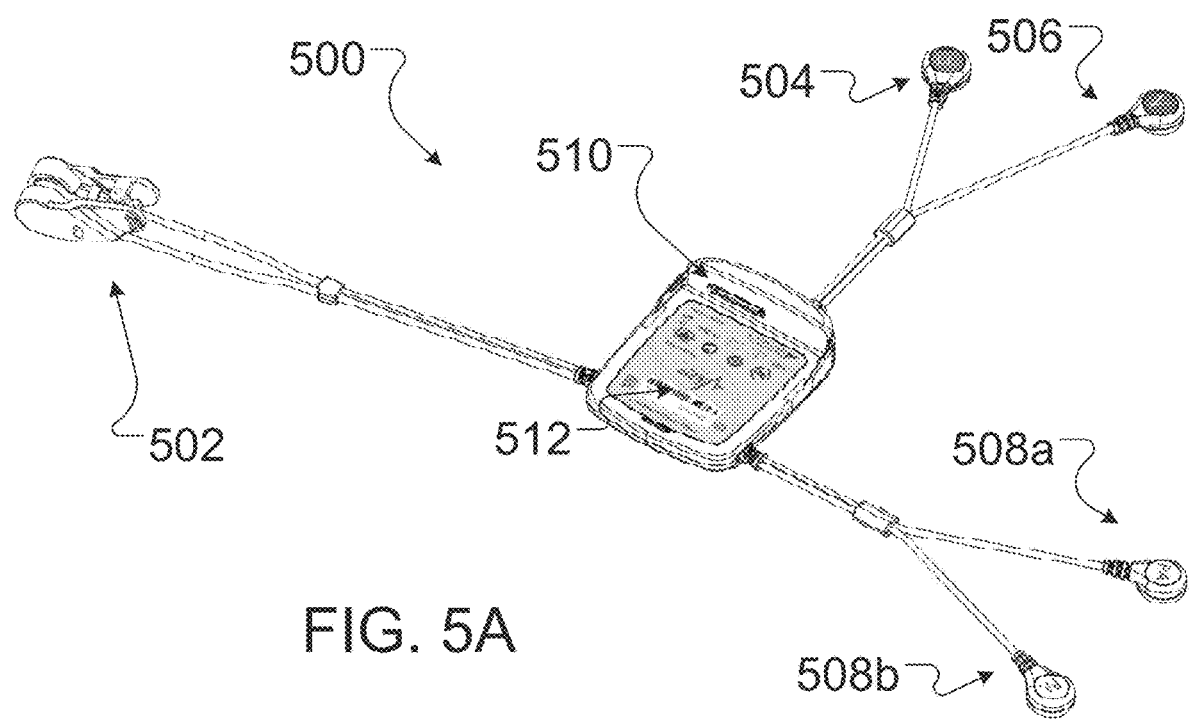
FIGS. 5A-5B show example embodiments of a patient worn sensor assembly.
Figure 5B:
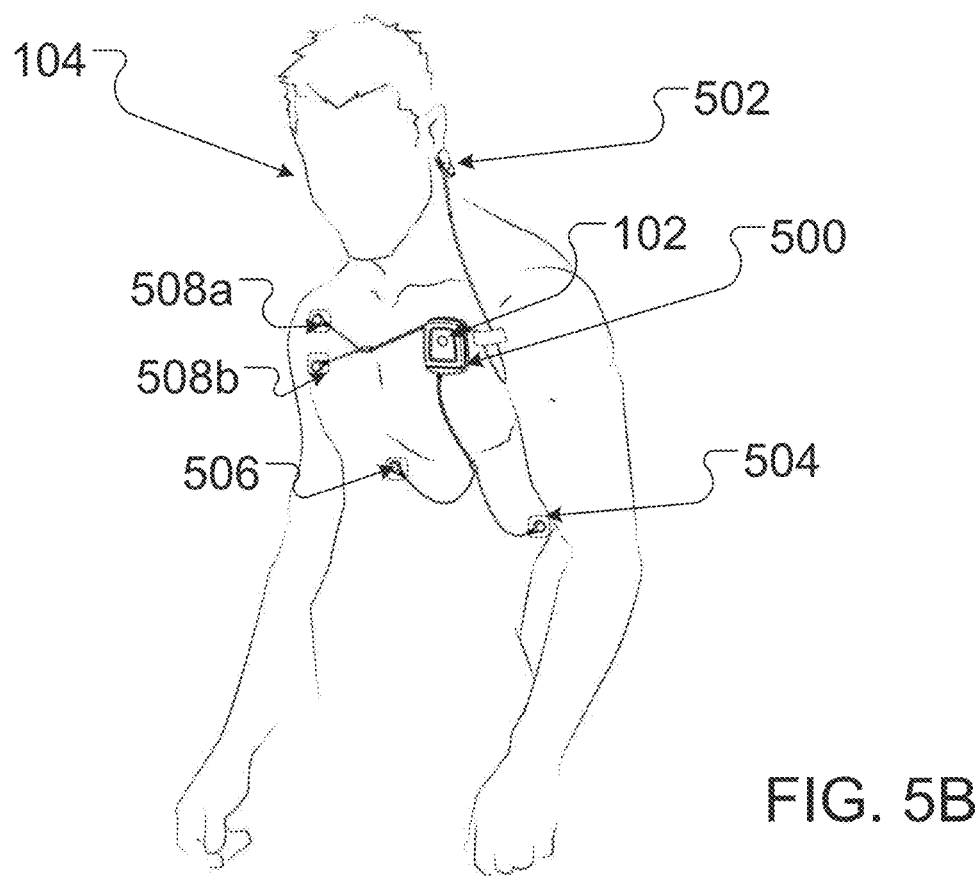

FIGS. 5A and 5B show example embodiments of a patient worn sensor assembly with an ear sensor 502. In particular, FIG. 5A is a perspective view of an adapter lead assembly 500 without a chest sensor attached. The adapter lead assembly 500 can form a portion of an alternative embodiment of the patient worn sensor assembly 200 when coupled with a chest sensor 102 described with respect to FIGS. 1, 2, 3A, and 3B. For example, the adapter lead assembly 500 can be configured to operatively connect to a chest sensor 102 through the connector 510. For example, the 30-pin male connector 204 of the chest sensor 102, can connect to a 30-pin female connector 510. In other embodiments, other types of connectors can be used other than 30-pin connectors, as described above. In some implementations, the adapter lead assembly 500 can be configured to be disposable and replaced by another electrode assembly having an identical or similar design to that of the adapter lead assembly 500, or replaced by an electrode assembly having a different design than the adapter lead assembly 500, such as the adapter lead assembly 400 described above. In some implementations, the adapter lead assembly 500 is reusable and is configured to operatively connect with one or more disposable electrode pads that are configured to affix to a patient's skin.

The adapter lead assembly 500 includes electrode leads 504, 506, 508A, and 508B, and an ear sensor 502. The ear sensor can be configured to measure SpO2 and pulse rate, vitals derived from pulse oximetry. The electrode leads 504, 506, 508A, and 508B can be configured to provide a multi-lead ECG. Each electrode lead includes connectors configured to operatively connect with electrode pads. For example, each of the electrode connectors can operatively connect with single electrode pads (for example, "red dot" ECG electrodes) that include electrodes having hydrogels for contacting a patient's skin and collecting vital signs and adhesive layers for securely affixing to the patient's skin. In some implementations, the two electrode connectors are positioned on the right side of a patient to collect vital sign information. The electrode leads 504, 506, 508A, and 508B for the adapter lead assembly 500 include electrically conductive material (e.g., one or more wires) that convey electrical signals from the electrode connectors to the main body (and eventually to a sensor, such as the sensor 102 of FIGS. 1-3).

FIG. 5B shows an example of a patient 104 using a patient worn sensor assembly, and in particular, shows adapter lead assembly 500 of FIG. 5A with chest sensor 102 operatively connected, and the ear sensor 502. The adapter lead assembly 500 is shown affixed to a patient 104. The adapter lead assembly 500 is affixed to a left upper chest portion of the patient 104 near the patients 104 heart.

FIG. 5B additionally shows electrode leads 504, 506, 508A, and 508B. For example, electrode leads 508A and 508B are positioned on the right side of the patients 104 chest to serve as "right arm" leads. FIG. 5B further shows the electrode lead 504 positioned on a left side of the patients 104 abdomen to serve as a "left leg" lead, and electrode lead 506 positioned on the center of the patients 104 abdomen near the sternum to serve as a precordial lead. In the example shown, each electrode lead 504, 506, 508A, and 508B are operatively connected to electrode pads. The electrode pads include electrodes for sensing patient vital signs and adhesive layers for affixing to the patients 104 skin.

In some implementations, the ear sensor 502 transfers information to the chest sensor 102 (e.g., through a wireless or wired connection) and the chest sensor 102 transfers information collected by ear sensor 502 to the bedside monitor 108 and transmits settings information and other information indicated by the bedside monitor 108 to the ear sensor 502. In some implementations, the ear sensor 502 also communicates with the bedside monitor 108 (e.g., through a wireless Bluetooth connection, other wireless connection, or through a wired connection).

Figure 6:
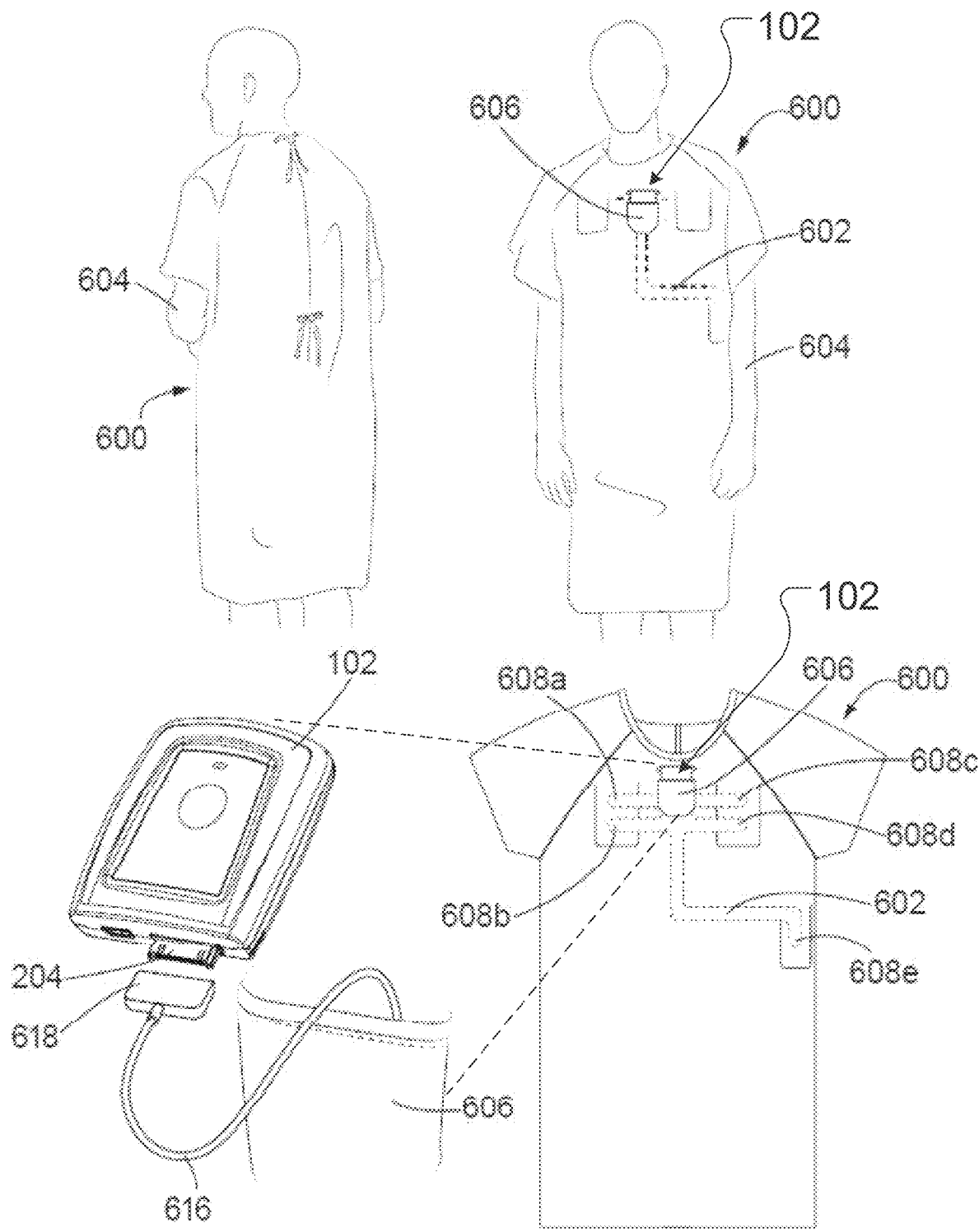
FIG. 6 shows an example embodiment of a garment that includes a sensor assembly.

FIG. 6 shows an example embodiment of a patient worn garment 600 (e.g., a medical gown such as the type generally worn in a hospital setting) having integrated therein (or alternatively, affixed thereto) a multi-layered lead assembly 602, such as sensor assembly 200 as described herein. Thus, instead of using the adapter lead assembly 400 or 500 described above, vital signs of a patient can be acquired by connecting the multi-layered lead assembly 602 attached to the patient worn garment 600 to chest sensor 102 to form a sensor lead assembly. As shown, the chest sensor 102 can connect to the multi-layered lead assembly 602 by electrically connecting to the adapter cable 616. The adapter cable 616 includes a 30-pin female connector 618 configured to connect to the 30-pin male connector 204 of the chest sensor 102. In other embodiments, other types of connectors can be used other than 30-pin connectors, as described above. The connectors 204 and 618 can be, for example, corresponding USB connectors, firewire connectors, lightning connectors, 30-pin connectors (such as, for example, a JAE 30 pin DD1 series connector), a custom proprietary connector, or any suitable connector that would be known to a person having ordinary skill in the art.

The patient worn garment 600 is configured to operatively connect various electrodes in contact with the skin of a patient 604 with a sensor assembly (not shown) that can be carried by or affixed to the garment (such as in a pocket 606 configured to hold the sensor as shown in FIG. 6). The electrodes can be, for example, ECG electrodes having gels that can contact the patient 604's skin and affix to the patient 604's skin to sense vital signs. Alternatively, the electrodes can be conductive material such as conductive rubber that can be, for example, integrated as part of the garment 600 and/or the multi-layered lead assembly 602. The electrodes can be either adhesive or non-adhesive. Extending portions of the multi-layered lead assembly 602 can be positioned within the garment 600 such that when the garment 600 is worn by a patient, the ends of extending portions 608a-e of the multi-layered lead assembly 602 are positioned so as to collect various vital sign measurements of the patient 604. For example, some or all of the extending portions 608a-e can be positioned such that they can connect to electrodes that are positioned on the patient 604's skin to serve as left arm, right arm, left leg, and right leg (ground) type electrodes.

For example, in some implementations, the extending portion 608a connects (e.g., releasably or permanently) with an ECG electrode gel, conductive rubber, or other type of electrode to form a "right arm" electrode. The extending portion 608b can connect (e.g., releasably or permanently) with an ECG electrode gel, conductive rubber, or other type of electrode to serve as an electrode that is used in a bio-impedance measurement. For example, the extending portion 608b in conjunction with an electrode in contact with the patient 604's skin can serve as a current injection electrode for use in a bio-impedance measurement. For example, the extending portion 608b in conjunction with an electrode in contact with the patient 604's skin can serve as a current injection electrode for a 4-point bio-impedance measurement in which a known value of current is injected into a patient and a pair of electrodes are used to measure the induced voltage, which can be used along with the known current value to calculate the bio-impedance.

The extending portion 608c can connect (e.g., releasably or permanently) with an ECG electrode gel, conductive rubber, or other type of electrode form a "left arm" electrode. The extending portion 608d can connect (e.g., releasably or permanently) with an ECG electrode gel, conductive rubber, or other type of electrode form a "right leg" (ground) electrode. The extending portion 608e can connect (e.g., releasably or permanently) with an ECG electrode gel, conductive rubber, or other type of electrode form a "left leg" electrode.

The pocket 606 of the garment 600 is configured/shaped to support and partially conceal the sensor 102. The pocket 606 can be configured to securely hold the sensor 102 close to the patient to minimize jostling or movement of the sensor 102 minimizing noise in the signals received from the multi-layered lead assembly 602.

Figure 7A:
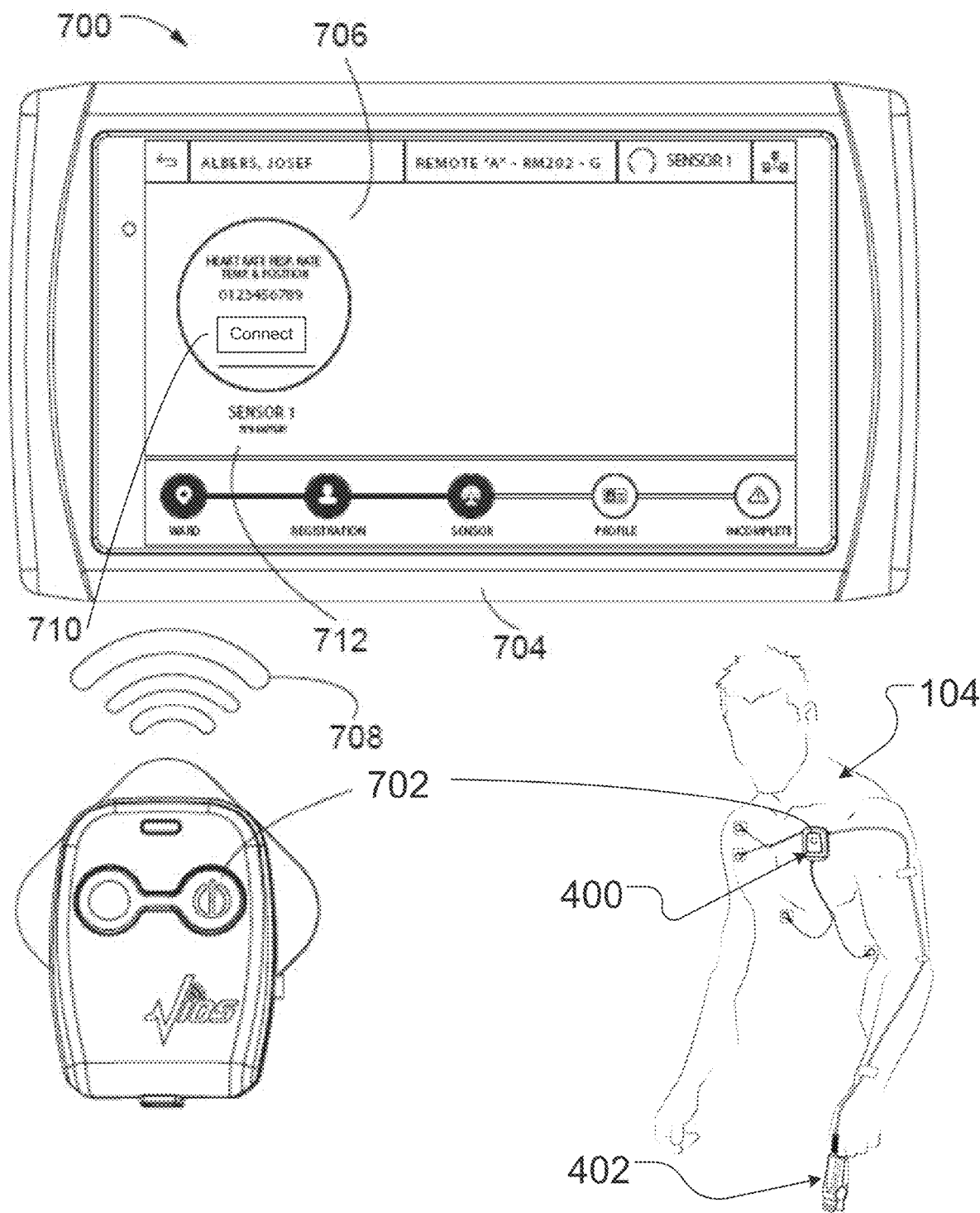
FIGS. 7A-7E show a patient worn sensor in wireless communication with a bedside monitor having example display screens for conveying sensor assembly and patient information.

FIGS. 7A-7E show a patient worn sensor in wireless communication with a bedside monitor and example display screens for conveying sensor assembly and patient information. In particular, FIG. 7A shows a system 700 that includes a patient worn sensor 702 in wireless communication with a bedside monitor 704 having a bedside monitor 704 (e.g., bedside monitor 108) displaying information for a patient care system, such as, for example, the system 100 of FIG. 1. FIG. 7A shows the patient worn sensor 702 connected to adapter lead assembly 400 and is shown as affixed to a patient 104. The adapter lead assembly 400 is affixed to a left upper chest portion of the patient 104 near the patients 104 heart. The adapter lead assembly 400, as described herein with reference to FIGS. 4A-4B, includes a finger sensor 402.

The bedside monitor 704 can include a user interface 706 that includes information received from the patient worn sensor 702 and/or information associated with a patient associated with the patient worn sensor 702. The patient worn sensor 702 can be, for example, a chest sensor such as the chest sensor 102 of FIG. 1. The patient worn sensor 702 can include contacts for attaching to the skin of a patient and recording various patient vital signs such as blood pressure, body temperature, respiratory rate, body impedance, blood oxygenation, heart rhythm (via ECG), and heart rate.

The patient worn sensor 702 can wirelessly communicate with the bedside monitor 704 through a wireless connection 708 using a wireless communication protocol such as, for example, Bluetooth, WiFi, or a cellular protocol. The patient worn sensor 702 can transmit vital sign information for the patient to the bedside monitor 704 through the wireless connection 708. In some implementations the patient worn sensor 702 can perform processing on the collected vital sign information prior to transmission of the information to the bedside monitor 704, while in some implementations, the patient worn sensor 702 can transmit raw vital sign information to the bedside monitor 704 instead of or in addition to processed information. The bedside monitor 704 is a touch screen device, such as a tablet, that is capable of receiving touch screen inputs. In some implementations, the bedside monitor 704 can receiving input from a keyboard, mouse, input buttons, or one or more devices capable of recognizing voice commands. In some implementations, the bedside monitor 704 is controlled using a device in wireless communication with the bedside monitor 704, such as a mobile phone. In some implementations, the bedside monitor 704 is a "headless" device that does not include direct user input and/or output functionality, but rather merely serves as a processing device for processing raw vital sign information received from the patient worn sensor 702, detecting alarm states, transmitting alerts to other devices in communication with the bedside monitor 704, and transmitting patient information to one or more central servers (e.g., the central server 113 of FIG. 1). In such cases, the bedside monitor 704 would not include a display.

The user interface 706 displays information for a patient "Josef Albers" associated with the patient worn sensor 702. At 710, the user interface 706 indicates that the patient worn sensor 702, having a sensor ID of 012346789 is synced with the bedside monitor 704 and is currently collecting information for the patient including heart rate, respiration rate, temperature, and patient position/location. The user interface 706 further indicates at 712 that the battery level for the patient worn sensor 702 (identified as "sensor 1" by the user interface 706) is 75%. The user interface 706 can further include selectable areas that can be used to sync additional sensors with the bedside monitor 704, or perform other functions. For example, a user can select to sync a patient worn sensor associated with a different patient with the bedside monitor 704.

A user of the bedside monitor 704 can use touchscreen functionality of the bedside monitor 704, a mouse, or another input device to select an area of the user interface 706 at 710 to cause additional display screens associated with the patient associated with the patient worn sensor 702 (displayed as "sensor 1") on the bedside monitor 704. In the example shown, selecting the user interface 706 at 710 can cause one or more additional display screens having information associated with the patient "Josef Albers" to be displayed.

Figure 7B:
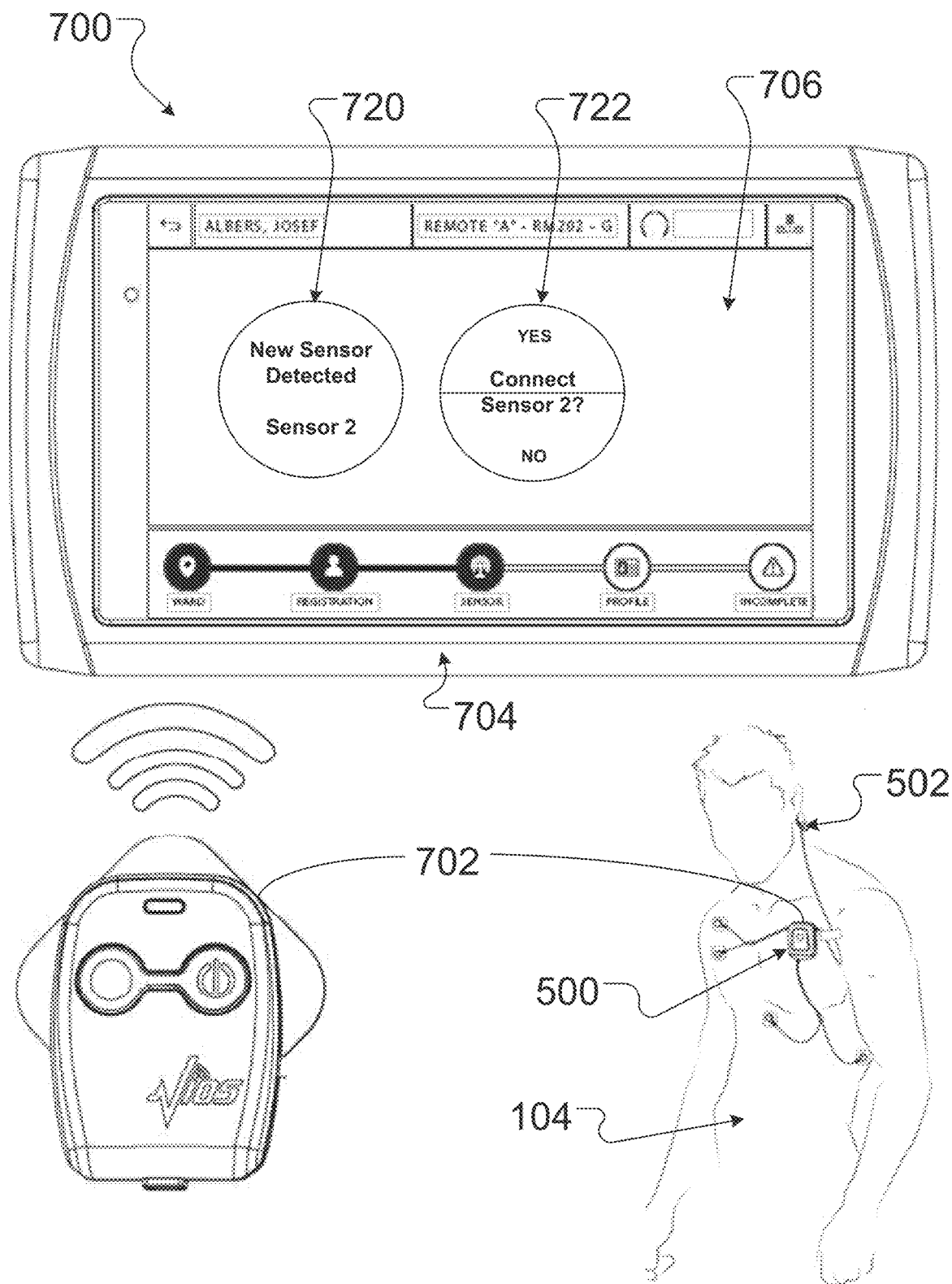

FIG. 7B shows a system 700 that includes a patient worn sensor 702 in wireless communication with a bedside monitor 704 having a bedside monitor 704 displaying information for a patient care system, such as, for example, the system 100 of FIG. 1. FIG. 7B shows the patient worn sensor 702 connected to adapter lead assembly 500 and is shown as affixed to a patient 104. The adapter lead assembly 500 is affixed to a left upper chest portion of the patient 104 near the patients 104 heart. The adapter lead assembly 500, as described herein with reference to FIG. 5, includes an ear sensor 502.

FIG. 7B is similar to FIG. 7A, except a different adapter lead assembly 500 has now been connected to the patient and the user interface 706 now includes interface elements 720 and 722. Assume, as an example, a healthcare practitioner desired to switch the adapter lead 400 as shown in FIG. 7A, to now using the adapter lead assembly 500. Once the adapter lead assembly 500 is connected to the chest sensor 702, the system can automatically detect that new adapter lead assembly has been connected through the processes described herein using the particular configuration resistance that is unique to the adapter lead assembly 500. In an exemplary implementation, the system would automatically display the customized vital sign measurements which pertains to the adapter lead assembly 500, which is an ECG sensor assembly with an oximeter sensor for the ear, as shown in FIG. 7C.

In some implementations, as shown in FIG. 7B, before the system automatically displays the vital sign information, the system can first prompt the healthcare practitioner to confirm that they intended to switch the sensor lead assembly. For example, as shown in FIG. 7B, an alert is shown to the user in interface element 720, notifying that a new adapter lead assembly has been connected (e.g., "Sensor 2"). Then selectable interface element 722 is shown to the user, allowing the user to select "Yes" or "No" as to whether to allow the bedside monitor 704 to connect to the new Sensor 2. If the user selects yes, then the user interface 706 will switch to an updated user interface that is configured for "Sensor 2," as shown in FIG. 7E. If no is selected, the user interface will return to the previous screen, or a screen with no measurements being taken since now the system is being told to not connect to the newly detected lead assembly.

In some implementations, if the system detects a new lead assembly attached, it will proceed and automatically switch the user interface 706 to the new configuration data screen to display the vital signs that correlate to the new lead assembly. For example, once adapter lead assembly 500 is electrically connected to the chest sensor 102, and the system analyzes and determine the configuration information for that particular lead assembly, the user interface can be automatically updated to the particular configuration user interface that was designed for that particular lead assembly. An example screenshot for a configuration for the adapter lead assembly 500 (i.e., an ECG sensor assembly with an ear pulse oximeter) is discussed below with reference to FIG. 7C FIG. 7C shows a system 700 that includes a patient worn sensor 702 in wireless communication with a bedside monitor 704 having a bedside monitor 704 displaying information for a patient care system, such as, for example, the system 100 of FIG. 1. FIG. 7C shows the patient worn sensor 702 connected to adapter lead assembly 500 and is shown as affixed to a patient 104. The adapter lead assembly 500 is affixed to a left upper chest portion of the patient 104 near the patients 104 heart. The adapter lead assembly 500, as described herein with reference to FIG. 5, includes an ear sensor 502.

Figure 7C:
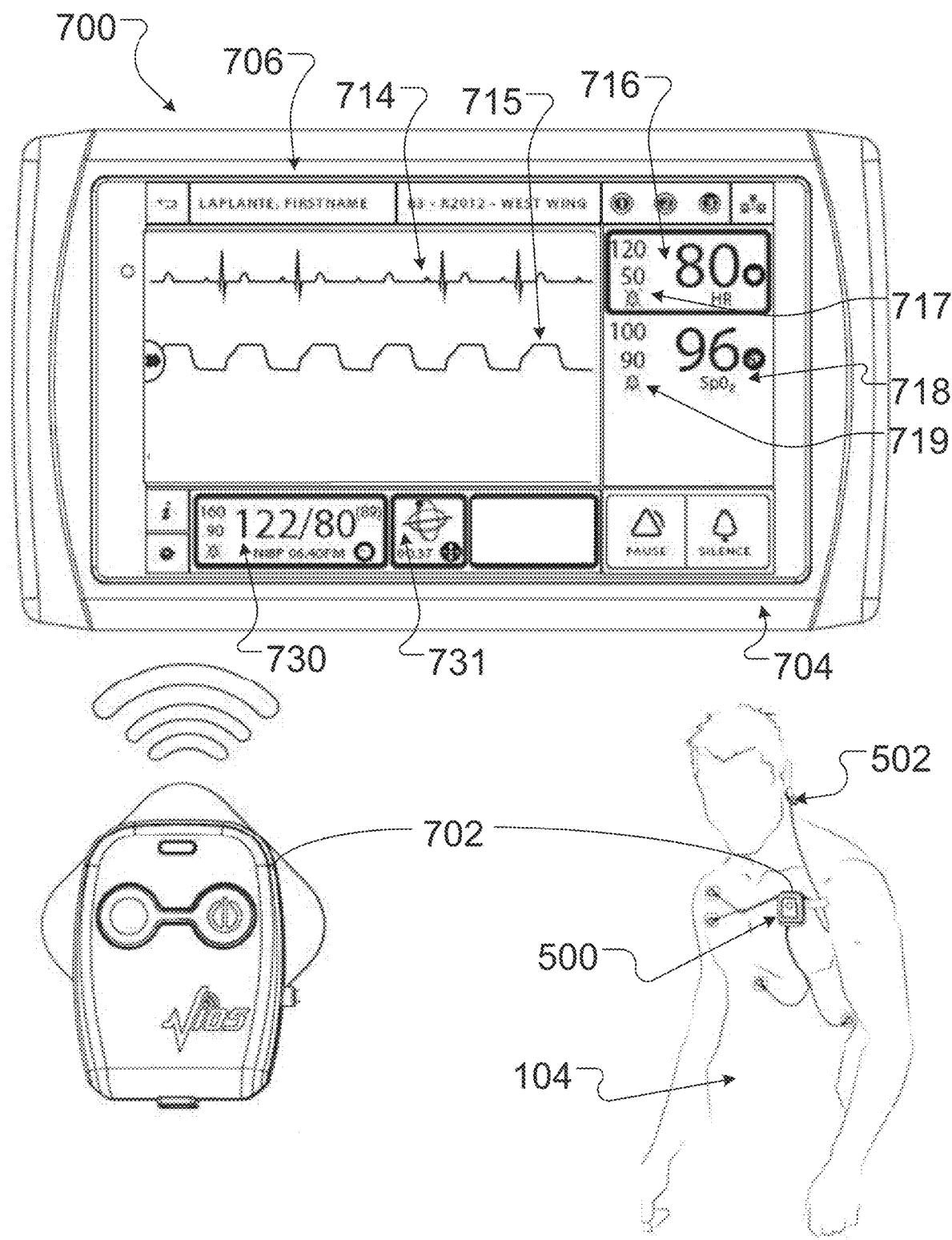

FIG. 7C is similar to FIG. 7B, using the same adapter lead assembly 500 with the ear sensor 502 as an oximeter, except the user interface 706 now includes vital sign measurement areas 714, 715, 716, 718, 730, and 731, among others. For example, after a health practitioner switched to the adapter lead assembly 500 in FIG. 7B, and accepted the lead assembly as the new sensor, the bedside monitor user interface 706 now automatically displays the customized vital sign measurements which pertain to the adapter lead assembly 500, which is a short lead ECG sensor assembly with an oximeter sensor for the ear.

The user interface 706 additionally shows various vital sign waves and numeric levels. For example, the user interface 706 shows a heart rate waveform 714 for the patient, as well as a numeric heart rate value for the patient at vital sign measurement area 716. In the example shown, the heart rate value for the patient is 80 beats per minute. The vital sign measurement area 716 indicates an acceptable heart rate level for the patient as falling between 50 and 120 beats per minute. Being as the current heart rate for the patient of 80 beats per minute falls within the indicated acceptable range, there is not currently an alarm state for heart rate for the patient. This is indicated by an icon 717 of a bell superimposed with an "X" symbol also within the vital sign measurement area 716. The icon 717 indicates that the current heart rate of the patient is within the acceptable range. In a situation in which the heart rate for the patient is not within the acceptable level, the icon 717 can change to indicate an alarm state. For example, the "X" can disappear from the icon 717 and the icon 717 can light up or flash to indicate an alarm state. Additionally, the bedside monitor 704 can emit an audible alarm to alert nearby caregivers to an alarm state for the patient. In some implementations, other portions of the user interface 706 can flash or otherwise indicate an alarm state. For example, the displayed heart rate value can flash when the patient's heart rate is outside of an acceptable level. In some implementations, the icon 717 (or other portions of the user interface 706) can flash at varying rates to indicate the severity of a particular alarm state. For example, the icon 717 can flash faster the further the patient's heart rate is from the acceptable range.

The user interface 706 also shows a blood oxygenation waveform 715 and a numeric blood oxygenation value for the patient at vital sign measurement area 718. The user interface 706 also shows an acceptable blood oxygenation range for the patient. The user interface 706 further includes an icon 719, similar to icon 717 discussed above, indicating that the blood oxygenation level for the patient is within the acceptable range (indicated by an "X" symbol superimposed over a bell, indicating that the alarm is "off").

Depending on the sensor assembly attached to the chest sensor 702, the user interface 706 can also display vital sign measurement area 730 for a blood pressure value for the patient. In the example shown, the blood pressure value indicates that the patient's current blood pressure is 122/80. The user interface 706 additionally includes an acceptable blood pressure range for the patient (e.g., "160" and "90"). The vital sign measurement area 730 further includes an icon indicating that the blood pressure for the patient is within the acceptable range (indicated by an "X" symbol superimposed over a bell, indicating that the alarm is "off").

The user interface 706 further includes an orientation indicator 731 indicating a current orientation for the patient as well as an indication of how long the patient has been in the current orientation. The orientation indicator 731 can help a caregiver to identify if the patient has been in a current orientation for longer than a preferred length of time. The orientation indicator 731 can also be used to indicate that the patient has fallen and is in need of assistance (e.g., through use of an audible or visual alarm, indicating that the alarm is "off").

Figure 7D:
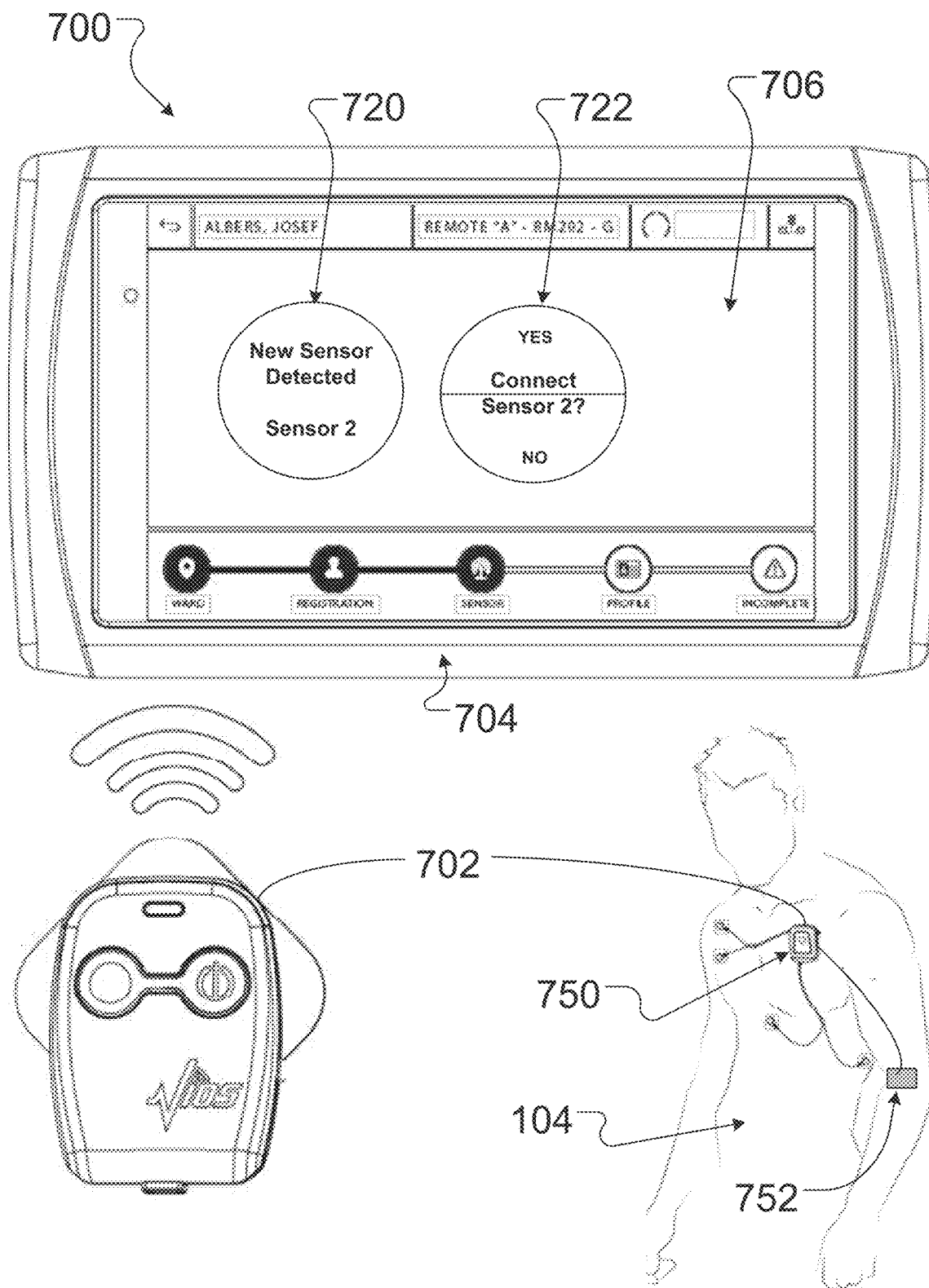
Figure 7E:
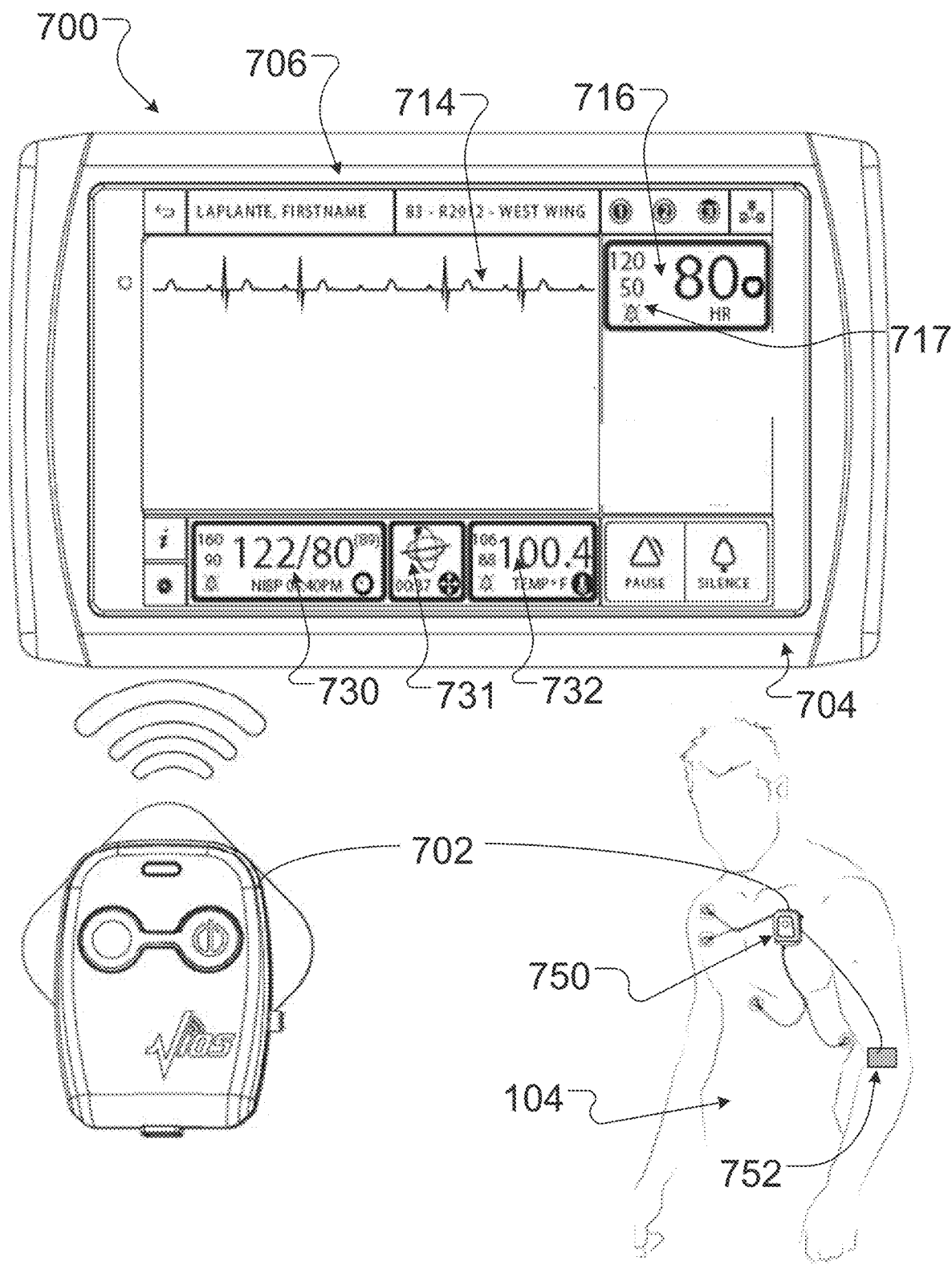

FIG. 7D shows a system 700 that includes a patient worn sensor 702 in wireless communication with a bedside monitor 704 having a bedside monitor 704 displaying information for a patient care system, such as, for example, the system 100 of FIG. 1. FIG. 7D shows the patient worn sensor 702 connected to adapter lead assembly 750 (an EKG configuration with a temperature sensor 752) and is shown as affixed to a patient 104. The adapter lead assembly 750 is affixed to a left upper chest portion of the patient 104 near the patients 104 heart.

FIG. 7D is similar to FIG. 7B, except a different adapter lead assembly 750 has now been connected to the patient and the user interface 706 switches to connecting to a new sensor workflow, which includes interface elements 720 and 722. Assume, as an example, a healthcare practitioner desired to switch the adapter lead assembly 500 as shown in FIGS. 7B and 7C (i.e., short lead EKG lead assembly with an ear sensor as the oximeter), to now using the adapter lead assembly 750 (i.e., short lead EKG lead assembly with a temperature sensor 752). Once the adapter lead assembly 750 is connected to the chest sensor 702, the system can automatically detect that new adapter lead assembly has been connected through the processes described herein using the particular configuration resistance that is unique to the adapter lead assembly 500. In an exemplary implementation, the system automatically displays the customized vital sign measurements which pertains to the adapter lead assembly 750, which is an ECG sensor assembly.

In some implementations, as shown in FIG. 7D, before the system automatically displays the vital sign information, the system can first prompt the healthcare practitioner to confirm that they intended to switch the sensor lead assembly. For example, as shown in FIG. 7B, an alert is shown to the user in interface element 720, notifying that a new adapter lead assembly has been connected (e.g., "Sensor 2"). Then selectable interface element 722 is shown to the user, allowing the user to select "Yes" or "No" as to whether to allow the bedside monitor 704 to connect to the new Sensor 2 (e.g., adapter lead assembly 750). If the user selects yes, then the user interface 706 will switch to an updated user interface that is configured for "Sensor 2," as shown in FIG. 7E. If no is selected, the user interface will return to the previous screen, or a screen with no measurements being taken since now the system is being told to not connect to the newly detected lead assembly.

FIG. 7E shows a system 700 that includes a patient worn sensor 702 in wireless communication with a bedside monitor 704 having a bedside monitor 704 displaying information for a patient care system, such as, for example, the system 100 of FIG. 1. FIG. 7E shows the patient worn sensor 702 connected to the adapter lead assembly 750 (i.e., a short lead EKG configuration with a temperature sensor 752, no oximeter) and is shown as affixed to a patient 104. The adapter lead assembly 750 is affixed to a left upper chest portion of the patient 104 near the patients 104 heart.

FIG. 7E is similar to FIG. 7D, using the same adapter lead assembly 750, except the user interface 706 now includes vital sign measurement areas 716, 730, 731, and 732, among others. For example, after a health practitioner switched to the adapter lead assembly 500 in FIG. 7B, and accepted the lead assembly as the new sensor, the bedside monitor user interface 706 now automatically displays the customized vital sign measurements which pertain to the adapter lead assembly 750, which is a short lead ECG sensor assembly with a temperature sensor 752.

The user interface 706 shows various vital sign waves and numeric levels. For example, similar to FIG. 7C, the user interface 706 shows the heart rate waveform 714 for the patient, as well as a numeric heart rate value for the patient at vital sign measurement area 716. The user interface 706 does not show a blood oxygenation waveform 715, or vital sign measurement area 718 for the numeric blood oxygenation value for the patient because now there is no oximeter (the ear sensor) attached to the lead assembly 750. The user interface 706 also displays vital sign measurement area 730 for a blood pressure value, and orientation indicator 731 indicating a current orientation for the patient as well as an indication of how long the patient has been in the current orientation.

Because the lead assembly 750 includes a temperature sensor 752, the user interface 706 includes a numeric body temperature value for the patient at vital sign measurement area 732. In the example shown, the body temperature value indicates that the patient's temperature is currently 100.4 degrees Fahrenheit. The vital sign measurement area 732 also includes an acceptable temperature range for the patient, and an icon indicating that the body temperature for the patent is within the acceptable range (indicated by an "X" symbol superimposed over a bell).

The user interfaces 706 as shown in FIGS. 7A-7E are not meant to be limiting to the examples as provided. The user interface 706 of the bedside monitor 704 can be programmed to display any number of vital sign measurements, alarms, indicators, and/or different user interfaces templates, depending on the sensing assembly. In some implementations, another type of apparatus may be used that can connect to the chest sensor 102 that includes a unique configuration resistor 220 in the adapter that connects to the chest sensor 102. For example, a testing assembly may be assigned a specific configuration resistor 220 in order to test components of the system, including the chest sensor 702 and the bedside monitor 704. Once an apparatus is connected to the chest sensor 702, the system can determine from the ADC measurement from the unique configuration resistor 220, a range values, and determine which configuration correlates with those specific range of values. Example processes of detecting the different configurations of the plurality of lead assemblies is provided below with reference to FIGS. 8 and 9.

Figure 8:
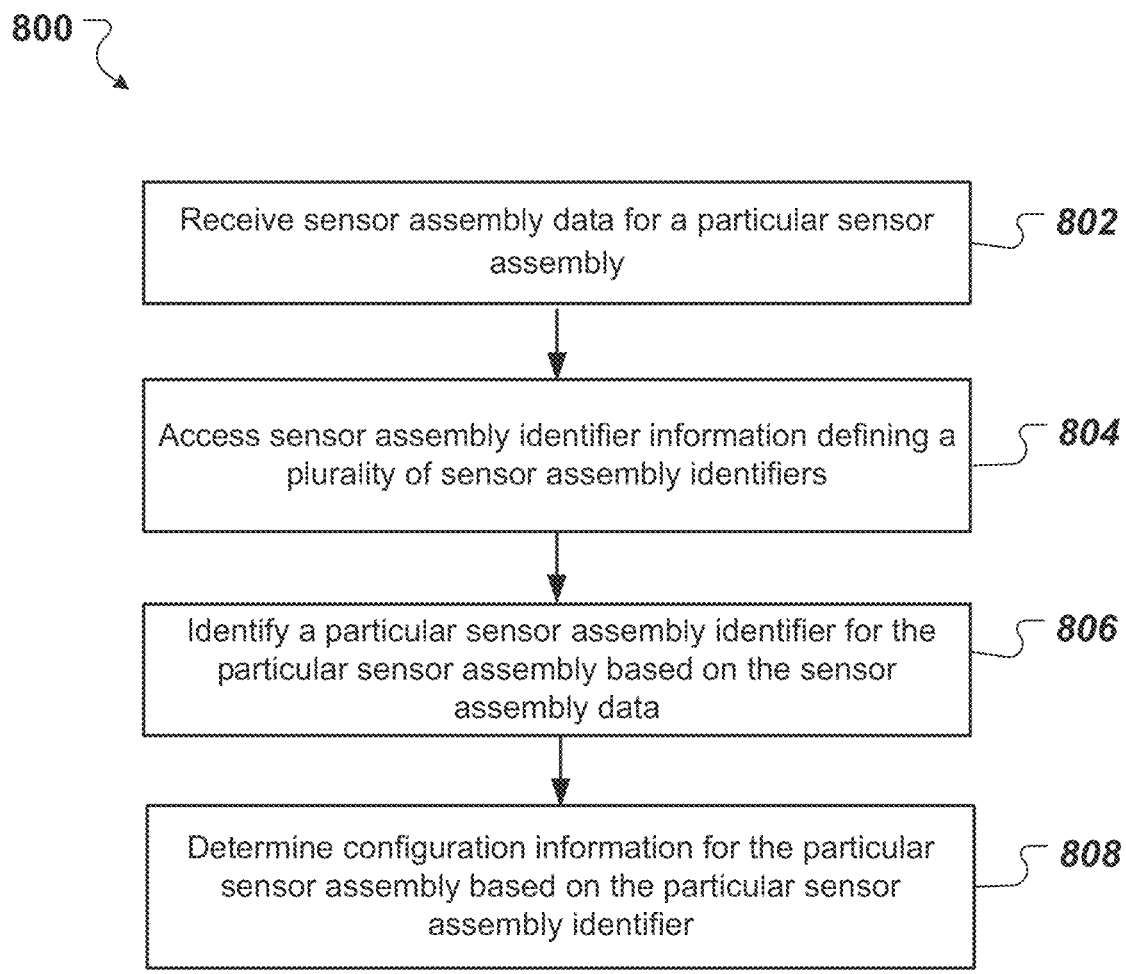
FIG. 8 is a flow diagram of an example process for identifying a sensor assembly configuration for a sensor assembly configured to be applied to the skin of a patient.

FIG. 8 is a flow diagram of an example process for identifying a sensor assembly configuration for a sensor assembly configured to be applied to the skin of a patient. The process 800 can be performed by the control processor 130 of the bedside monitor 108 or in any appropriate data processing apparatus. Operations of the process 800 can be implemented as instructions stored on a non-transitory computer readable medium, and execution of the instructions by one or more data processing apparatus can cause the one or more data processing apparatus to perform the operations of the process 800.

The process 800 includes receiving sensor assembly data for a particular sensor assembly (802). In some implementations, the control processor 130 of the bedside monitor 108 can receive data from the chest sensor 102. For example, the data can include the ADC values from the measured voltage of the ADC circuit 120 from the resistive voltage divider formed by the configuration resistor and an internal reference resistor in the chest sensor. The data can be sent from the chest sensor 102 to the bedside monitor 108 through the wireless communication units 122 and 132. The ADC values can be inserted into the protocol data stream for transmission to the bedside monitor 108.

According to some implementations, the sensor assembly data includes a measured voltage output from a resistive voltage divider formed by a configuration resistor and an internal reference resistor when a reference voltage is applied, wherein the configuration resistor is unique for each respective sensory assembly. In some implementations, the sensor assembly data includes resistor data specifying a particular resistance.

The process 800 further includes accessing sensor assembly identifier information defining a plurality of sensor assembly identifiers (804). For example, the control processor 130 of the bedside monitor 108 can access the sensor assembly identifier information from the storage unit 134. In some implementations, the storage unit 134 stores mapping data that includes associated values between the measured voltage output and an adapter assembly identifier. For example, the storage unit 134 stores configuration data for a range of ADC values that is associated with a particular configuration. In some implementations, the storage unit 134 can receive updated configuration data when the bedside monitor 108 receives updated data from a service technician, or through an automatic service update if the bedside monitor 108 is connected to an external network.

The process 800 further includes identifying a particular sensor assembly identifier for the particular sensor assembly based on the sensor assembly data (806). For example, the control processor 130 of the bedside monitor 108 can identify the sensor assembly identifier information after accessing the storage unit 134 based on the ADC value information received from the ADC circuit 120 of the chest sensor 102.

The process 800 further includes determining configuration information for the particular sensor assembly based on the particular sensor assembly identifier (808). In some implementations, the configuration information includes a number of leads for the particular sensor assembly. In some implementations, the configuration information includes a type of harness configuration for the particular sensor assembly. Additionally, or alternatively, the configuration information can include any type of information required by the sensor assembly that the healthcare practitioner desires and that bedside monitor can provide. For example, each unique configuration can specify a number of ECG leads, the type(s) of sensors attached to the sensor assembly, mapping of measurements to ECG leads and associated calculations, display content of specific waveforms, arrangement, and grayed out options, and signal processing coefficients. Thus, the control processor 130 of the bedside monitor 108 is configured to, after identifying the particular sensor assembly that is connected to the chest sensor, determine the specific configuration for the bedside monitor 108 and how to the receive data from the chest sensor 102 (e.g., the number of leads or type of measurement), how to analyze the data (e.g., signal processing coefficients), and/or how to display the data (e.g., UI layouts).

In some implementations, the sensor assembly is an electrode assembly configured to be applied to the skin of a patient. Alternatively, other sensing devices or apparatus could be used to determine configuration information for the particular sensor assembly. For example, the process of using an identifier could be used for other devices in a healthcare setting, or may be used outside of the healthcare setting, such as industrial. Any setting that uses different type of configurations of sensors, and that would benefit a quick plug-and-play type of connection to central unit, could be applied to process 800. For example, a mobile device using networking through WiFi or Bluetooth technology in order to quickly connect to other sensing devices, such as water meter's for utility companies.

Figure 9:
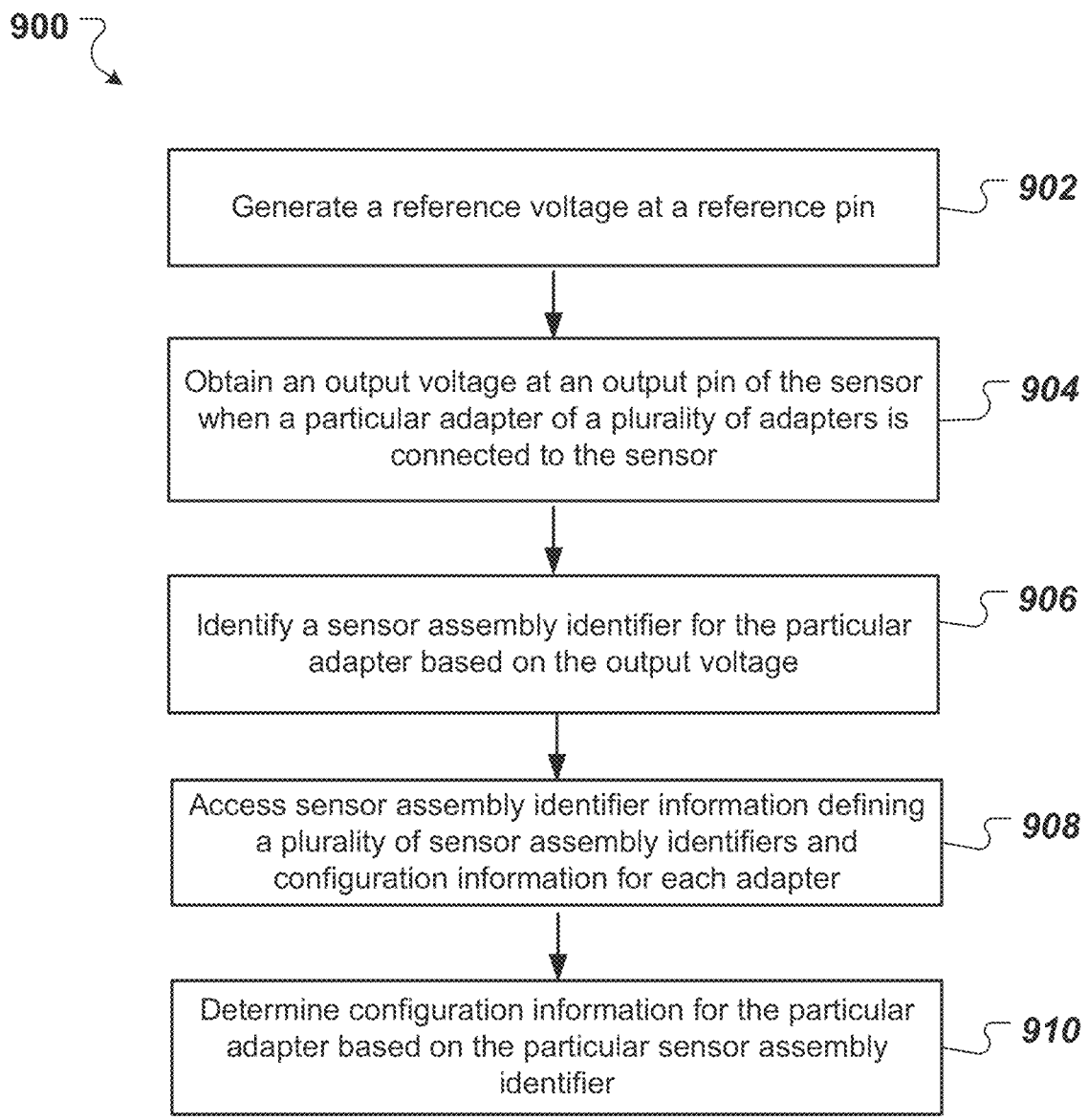
FIG. 9 is a flow diagram of an example process for identifying a sensor assembly configuration for a sensor assembly configured to be applied to the skin of a patient.

FIG. 9 is a flow diagram of an example process for identifying a sensor assembly configuration for a sensor assembly configured to be applied to the skin of a patient. The process 900 can be performed by the control processor 124 of the chest sensor 102 or in any appropriate data processing apparatus. Operations of the process 900 can be implemented as instructions stored on a non-transitory computer readable medium, and execution of the instructions by one or more data processing apparatus can cause the one or more data processing apparatus to perform the operations of the process 900.

The process 900 includes generating a reference voltage at a reference pin (902). For example, as shown in FIG. 3, a reference voltage ($V_{REF}$) is generated at the sensor 102, and is electrically connected thru an internal reference resistor 121 to a reference voltage pin 125.

The process 900 further includes obtaining an output voltage at an output pin of the sensor when a particular adapter of a plurality of adapters is connected to the sensor (904). For example, as shown in FIG. 3, an output voltage ($V_{OUT}$) can be measured by the ADC circuit 120 at pin 121 of the sensor 102 when the sensor 102 is electrically connected to the adapter lead assembly 202 when the electrical connection goes to ground thru a configuration resistor 121 in the adapter lead assembly 202. The electrical circuit connection is made when pin 125 of the sensor 102 is connected to pin 225 of the adapter lead assembly 202, and pin 121 of the sensor 102 is connect to pin 221 of the adapter lead assembly 202. The ADC circuit 120 is configured to measure a voltage output from a resistive voltage divider formed by the configuration resistor 220 and the internal reference resistor 121 when a reference voltage is applied when the adapter lead assembly 202 is connected to the sensor 102.

The process 900 further includes identifying a sensor assembly identifier for the particular adapter based on the output voltage (906). For example, the control processor 124 of the chest sensor 102 can identify the sensor assembly identifier based on the ADC value information received from the ADC circuit 120 of the chest sensor 102. Because obtaining the ADC output value from the ADC circuit 120 for converting the voltage measurement to an analog measurement, component tolerance and measurement noise can cause specific configurations to be represented by a range of values rather than one value. The specific configuration can be set by case ranges, where each range defines application specific parameters. Thus, the control processor 124 of the chest sensor 102 can identify the sensor assembly identifier as one value within a change of values. For example, a measured ADC value between 153 (low) and 161 (high), may be used for particular configuration, such as harness with ECG and temperature sensors.

The process 900 further includes accessing sensor assembly identifier information defining a plurality of sensor assembly identifiers and configuration information for each adapter (908). For example, the control processor 124 of the chest sensor 102 can access the sensor assembly identifier information from the storage unit 126, as discussed above with reference to FIG. 3B. In some implementations, the storage unit 126 stores mapping data that includes associated values between the measured voltage output and an adapter assembly identifier. For example, the storage unit 126 stores configuration data for a range of ADC values that is associated with a particular configuration. In some implementations, the storage unit 126 can receive updated configuration data when the bedside monitor 108 receives updated data from a service technician, or through an automatic service update if the bedside monitor 108 is connected to an external network, and the bedside monitor 108 sends the updated information to the control processor 124 of the chest sensor 102.

The process 900 further includes determining configuration information for the particular adapter based on the particular sensor assembly identifier (910). For example, the control processor 124 of the chest sensor 102 can first determine the configuration information, and send the configuration to the bedside monitor 108 through communication units 122 and 132. In some implementations, the configuration information includes a number leads for the particular sensor assembly. In some implementations, the configuration information includes a type of harness configuration for the particular sensor assembly (e.g., a body worn sensor configuration, a garment sensor configuration, a type of garment sensor, etc.). Additionally, or alternatively, the configuration information can include any type of information required by the sensor assembly that the healthcare practitioner desires and that bedside monitor can provide. For example, each unique configuration can specify a number of ECG leads, the type(s) of sensors attached to the sensor assembly, mapping of measurements to ECG leads and associated calculations, display content of specific waveforms, arrangement, and grayed out options, and signal processing coefficients. Thus, the control processor 124 of the chest sensor 102 is configured to, after identifying the particular sensor assembly that is connected to the chest sensor, determine the specific configuration for the bedside monitor 108 to the receive data from the chest sensor 102 (e.g., the number of leads or type of measurement), to analyze the data (e.g., signal processing coefficients), and/or to display the data (e.g., UI layouts) in a particular manner.

Thus, particular embodiments of the subject matter have been described. Other embodiments are within the scope of the following claims. In some cases, the actions recited in the claims can be performed in a different order and still achieve desirable results.

What is claimed is:

1. A system for detecting a configuration for a patient worn sensor assembly, the system comprising:
    a sensor assembly including:
        an adapter including a configuration resistor; and
        a sensor device including:
            an internal reference resistor;
            an analog-to-digital (ADC) circuit to measure a measured voltage output from a resistive voltage divider defined by the configuration resistor and the internal reference resistor when a reference voltage is applied;
            a first communicator to generate sensor device communication data, the sensor device communication data includes a sensor assembly identifier;
            a storage to store mapping data, the mapping data including associated values between the measured voltage output and the sensor assembly identifier; and
            a controller operably coupled to the storage and configured or programmed to identify the sensor assembly based on the mapping data and the measured voltage output; and
    a patient monitoring device communicatively coupled to the sensor assembly via the first communicator of the sensor device, the patient monitoring device including a second communicator to receive the sensor device communication data, including the sensor assembly identifier, from the first communicator of the sensor device.

2. The system of claim 1, wherein the mapping data is associated with a first range of measured voltage outputs indicative of the configuration resistor.

3. The system of claim 2, wherein
    the mapping data includes a plurality of ranges of measured voltage outputs,
    the plurality of ranges of measured voltage outputs includes the first range of measured voltage outputs,
    each range of the plurality of ranges of measured voltage outputs is associated with different configuration data of a respective sensor assembly of a plurality of the sensor assemblies, and
    each respective sensor assembly of the plurality of sensor assemblies includes a unique configuration resistor.

4. The system of claim 3, wherein
    the sensor assembly is a particular sensor assembly of the plurality of sensor assemblies, and
    the patient monitoring device determines, based on configuration data of the particular sensor assembly, application specific parameters of the particular sensor assembly.

5. The system of claim 4, wherein the application specific parameters include a number of leads of the particular sensor assembly.

6. The system of claim 4, wherein
    the patient monitoring device further includes a display, and
    the application specific parameters include graphical display data that specifies graphical contents to be displayed on the display of the patient monitoring device.

7. The system of claim 4, wherein the application specific parameters include a type of harness configuration of the particular sensor assembly.

8. The system of claim 1, wherein the sensor device and the adapter are releasably connected.

* * * * *